(12) United States Patent
Valero et al.

(10) Patent No.: US 9,513,372 B2
(45) Date of Patent: Dec. 6, 2016

(54) AUTOMATIC PROCESSING OF ULTRASONIC DATA

(71) Applicant: Schlumberger Technology Corporation, Sugar Land, TX (US)

(72) Inventors: Henri-Pierre Valero, Yokohama (JP); Adam Pedrycz, Yokohama (JP); Takeo Fujihara, Machida (JP)

(73) Assignee: Schlumberger Technology Corporation, Houston, TX (US)

( * ) Notice: Subject to any disclaimer, the term of this patent is extended or adjusted under 35 U.S.C. 154(b) by 361 days.

(21) Appl. No.: 13/943,791

(22) Filed: Jul. 17, 2013

(65) Prior Publication Data

US 2014/0204700 A1    Jul. 24, 2014

Related U.S. Application Data

(60) Provisional application No. 61/755,367, filed on Jan. 22, 2013.

(51) Int. Cl.
  *G01S 15/00*    (2006.01)
  *G01V 1/48*    (2006.01)

(52) U.S. Cl.
  CPC ............... *G01S 15/006* (2013.01); *G01V 1/48* (2013.01)

(58) Field of Classification Search
  CPC ......... G01S 15/00; G01S 15/006; G01S 15/02
  See application file for complete search history.

(56) References Cited

U.S. PATENT DOCUMENTS

| | | | | | |
|---|---|---|---|---|---|
| 4,052,889 | A | * | 10/1977 | Mucciardi et al. | 73/602 |
| 4,170,142 | A | * | 10/1979 | Posakony et al. | 73/603 |
| 4,274,288 | A | * | 6/1981 | Tittmann et al. | 73/602 |
| 2002/0099290 | A1 | * | 7/2002 | Haddad | 600/443 |

* cited by examiner

*Primary Examiner* — Luke Ratcliffe
*Assistant Examiner* — Hovhannes Baghdasaryan
(74) *Attorney, Agent, or Firm* — Daryl R. Wright; Jody Lynn Destefanis

(57) ABSTRACT

An example method for automatically characterizing an echo contained in an ultrasonic signal generated with an ultrasonic transducer can include receiving data corresponding to the ultrasonic signal, calculating an energy ratio of the ultrasonic signal and localizing the echo using the energy ratio. The method can include windowing a portion of the ultrasonic signal around the localized echo and calculating a Fast Fourier Transform (FFT) and a Hilbert envelop of the windowed portion. The method can include estimating M echo parameters from the FFT and the Hilbert envelope of the windowed portion, where each of the M parameter vectors includes a plurality of echo parameters, calculating M parametric echo models based on each of the M echo parameter vectors and iteratively minimizing a difference between the windowed portion of the ultrasonic signal and a sum of the M parametric echo models.

18 Claims, 23 Drawing Sheets

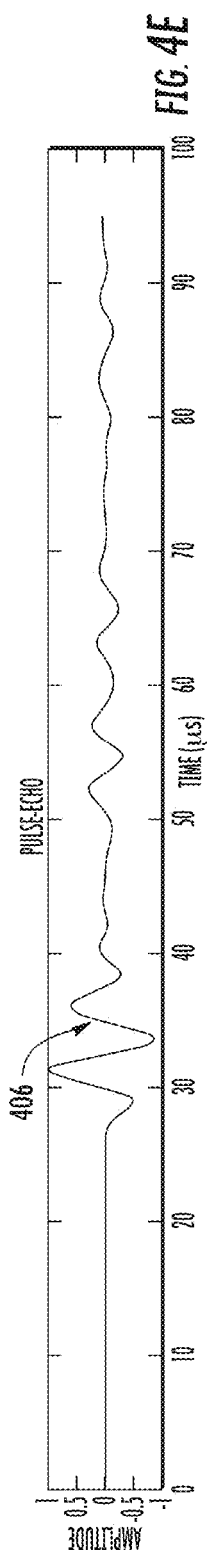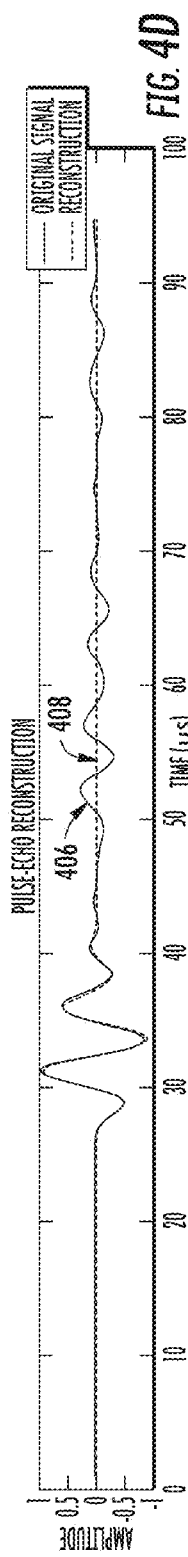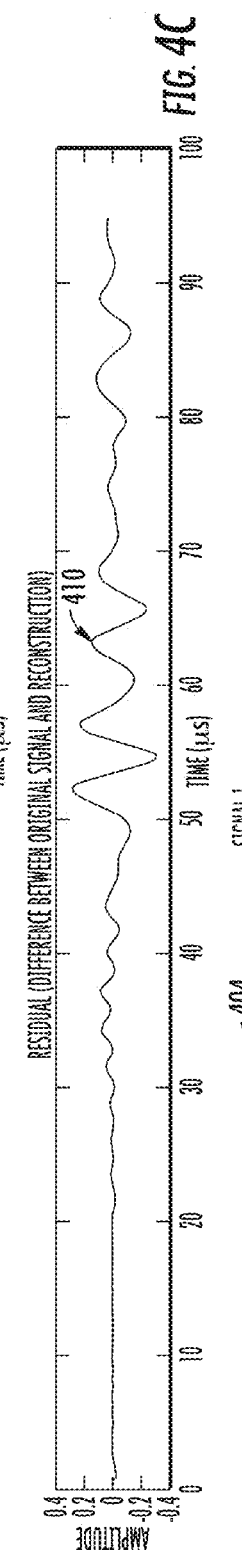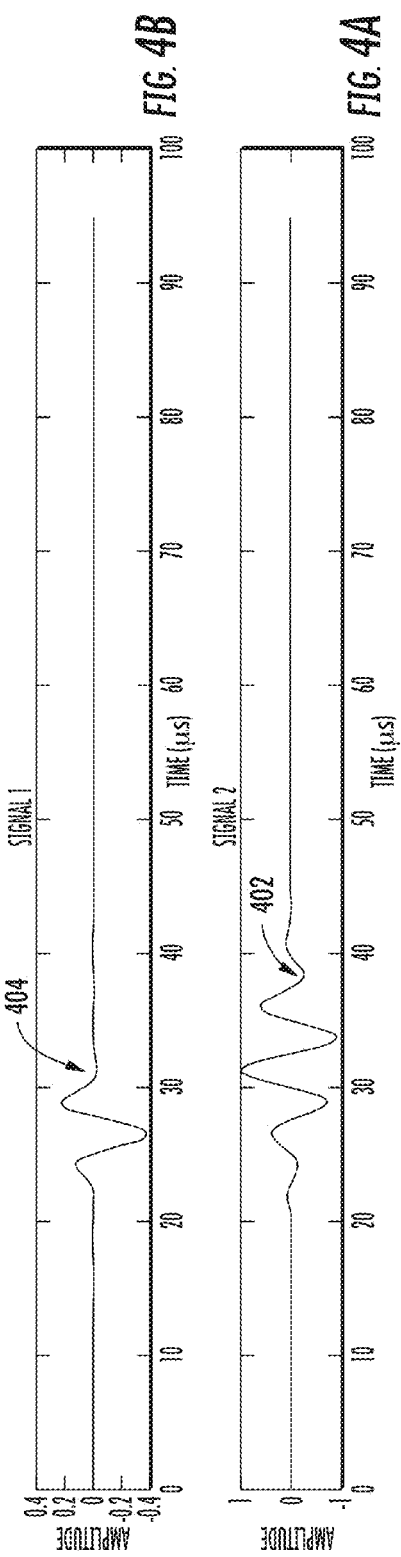

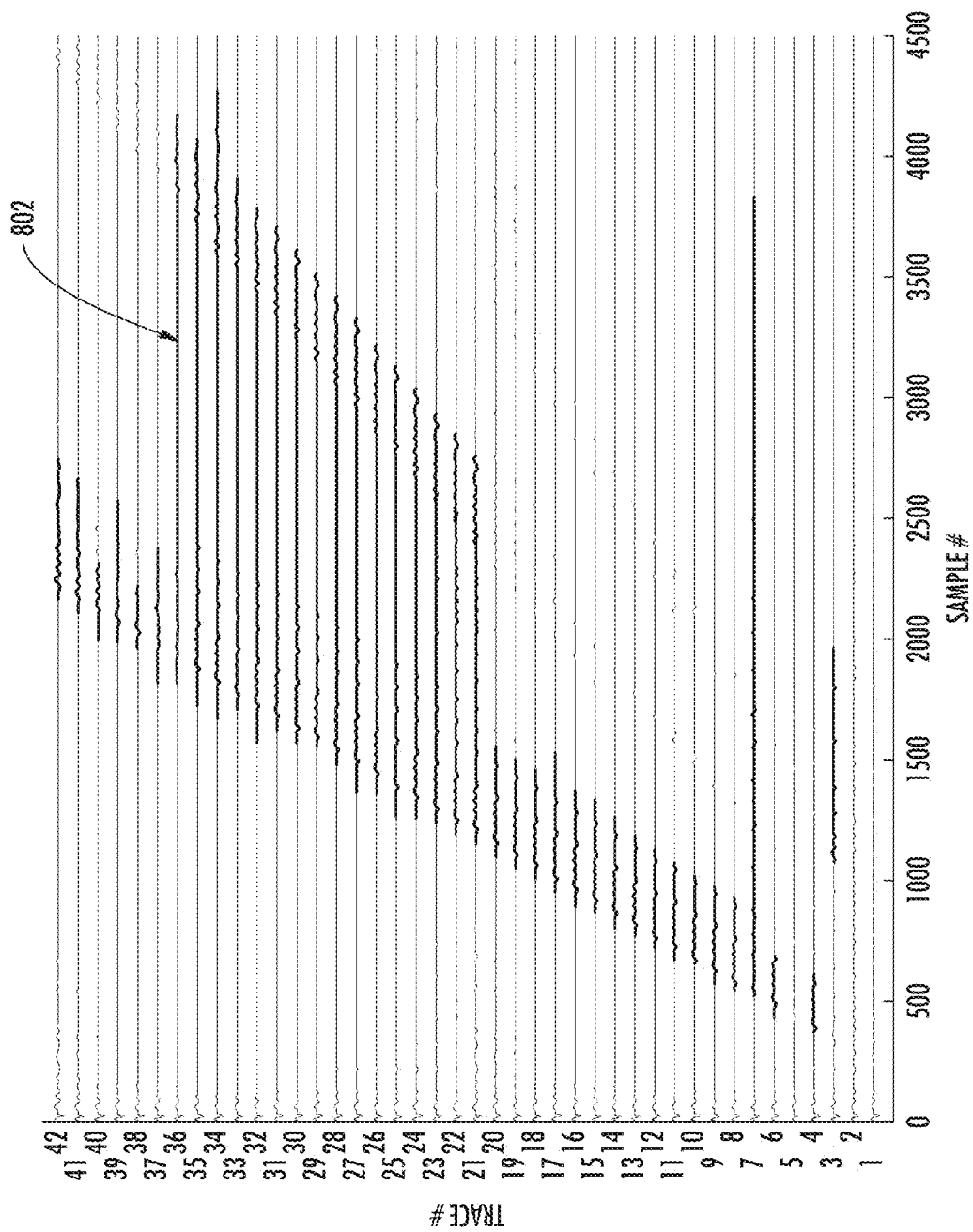

BOREHOLE DATA (SINGLE TRACE)
| OPTIMAL PARAMETERS | | | | |
|---|---|---|---|---|
| | BANDWIDTH FACTOR (MHz$^2$) | ARRIVAL TIME ($\mu$s) | CENTER FREQUENCY (MHz) | PHASE (rad) | AMPLITUDE (V) |
| MODEL #1 | 0.0323 | 67.3172 | 0.2580 | 9.8577 | 1.2645 |
| MODEL #2 | 0.0071 | 73.4771 | 0.2134 | 15.5138 | 0.5892 |
| MODEL #3 | 0.0907 | 60.3085 | 0.2361 | -0.6622 | 0.8540 |
FIG. 13A
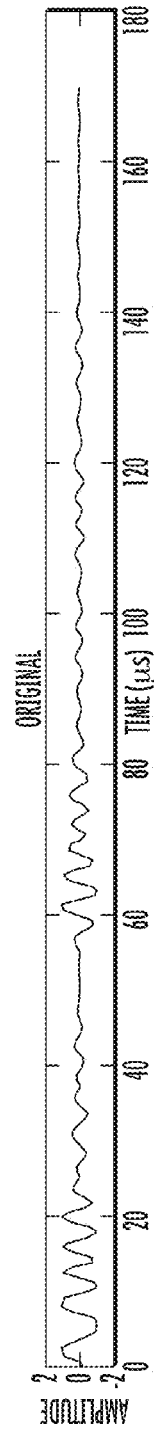
ORIGINAL
FIG. 13B
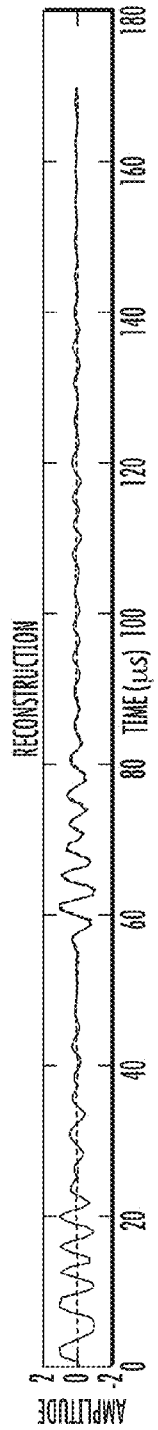
RECONSTRUCTION
FIG. 13C
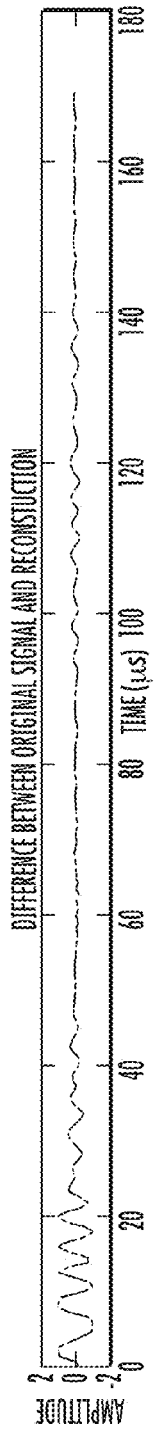
DIFFERENCE BETWEEN ORIGINAL SIGNAL AND RECONSTRUCTION
FIG. 13D

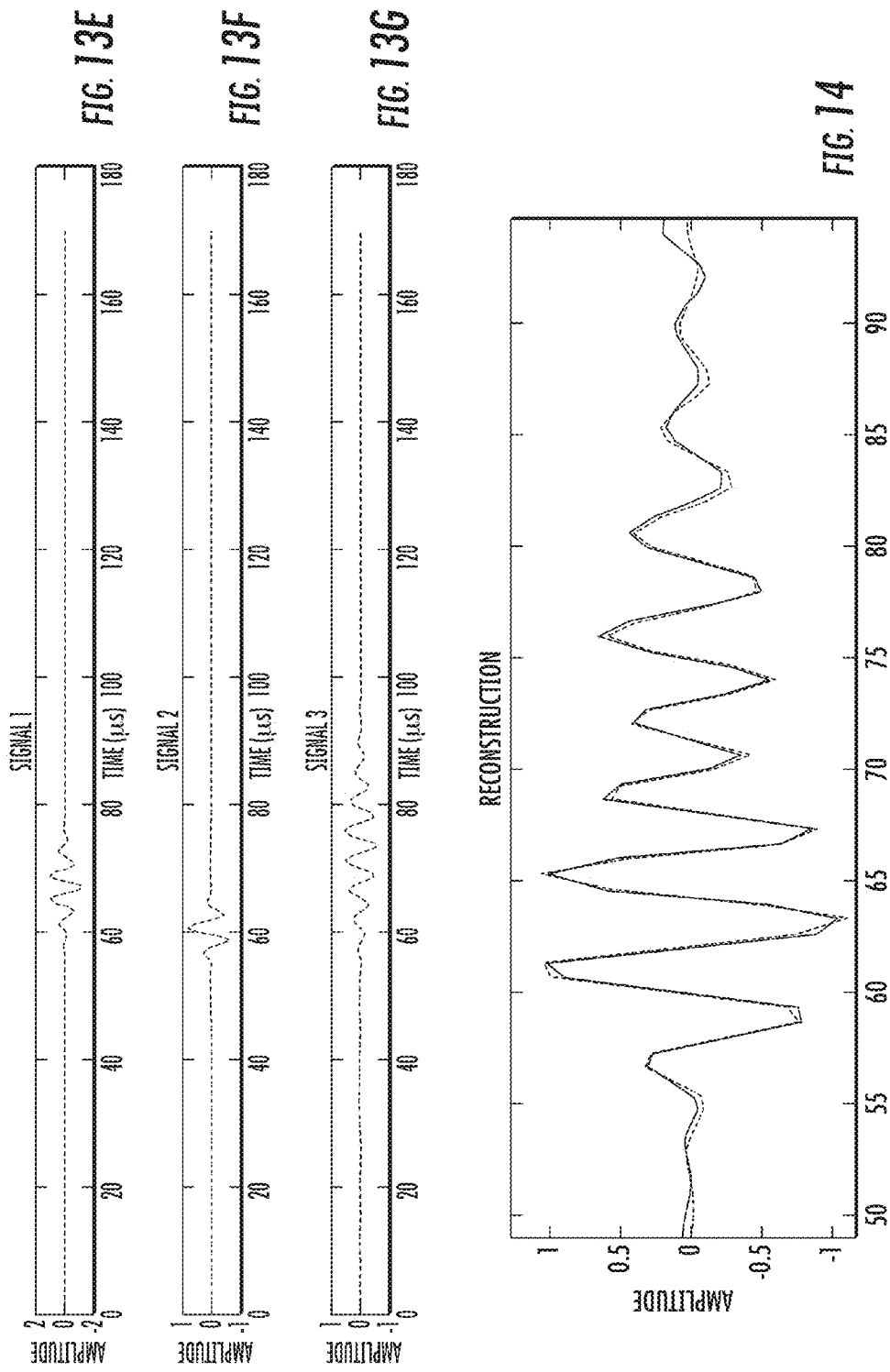

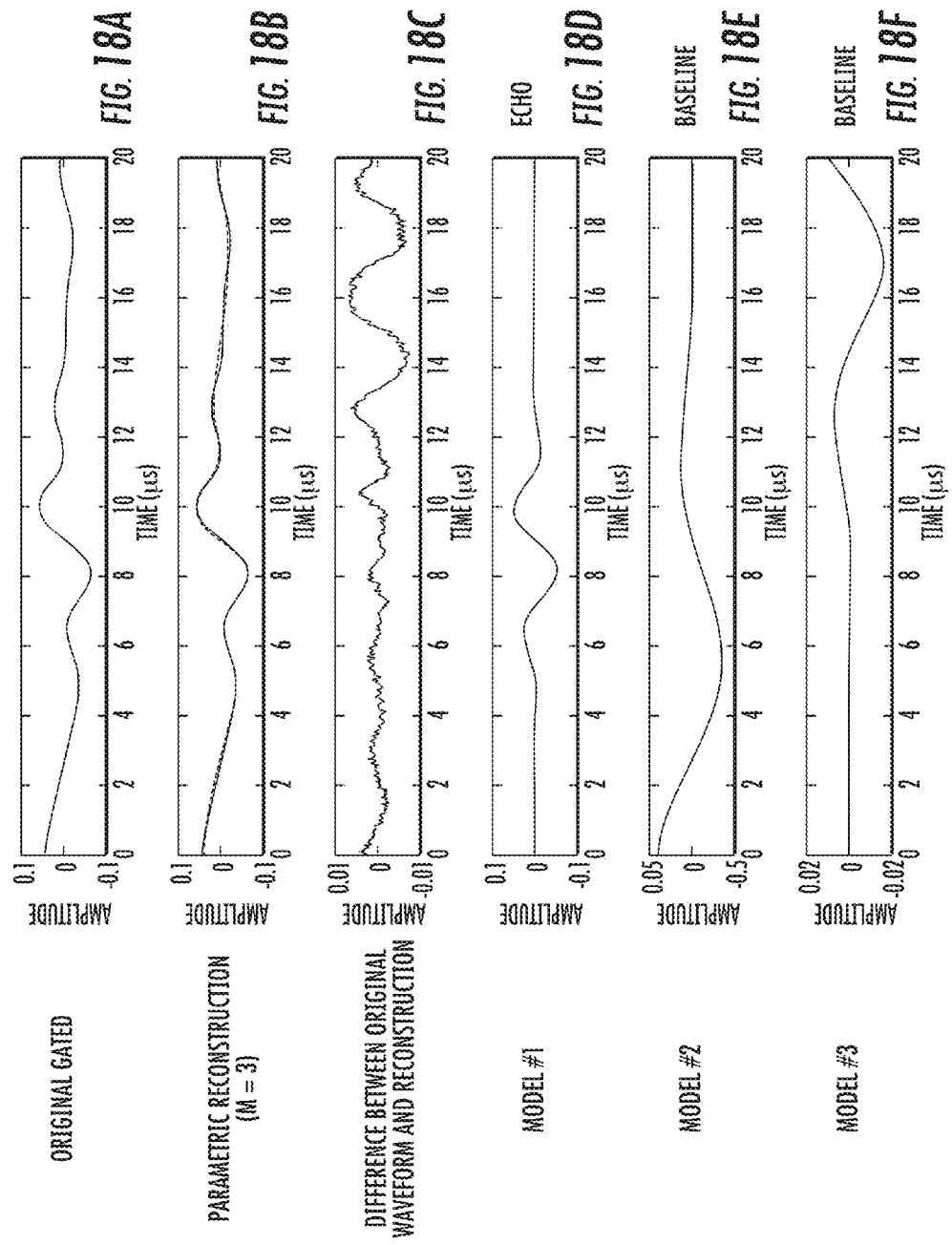

AUTOMATIC PROCESSING OF ULTRASONIC DATA

BACKGROUND

Ultrasonic non-destructive evaluation (NDE) is a widely used technology used to evaluate quantitative properties of unknown surfaces such as thickness, shape, and texture. In ultrasonic pulse-echo methods, back-scattered echoes from the surface contain essential information pertaining to the properties of the reflector. Thus, it is desirable to correctly extract this information (e.g., in terms of amplitude, arrival time and center frequency). The parameters for time of arrival, amplitude and center frequency have been widely used in ultrasonic applications. For example, a technique in which backscattered echoes are modeled as superimposed Gaussian echoes corrupted by noise is known in the art. Additionally, Expectation Maximization (EM)-based algorithms for estimating ultrasonic signals have been developed. EM-based algorithms use the Gauss-Newton or the Levenberg-Marquart method to conduct an optimization search which is subject to the pitfall of landing in local minima.

To improve the success of these techniques, a suitable initial guess must be made for the parameters of the echo being sought. In many cases, the echo to be characterized is obscured by noise or a noisy baseline, which makes it difficult to form the initial guess. In response, there have been various pursuits centered around denoising a signal to facilitate easier characterization of the echo. A significant portion of these initiatives use first-order statistical methods such as averaging (e.g., stacking) to produce an estimate of a noisy baseline that contaminates a signal. First-order statistical methods work well to estimate a baseline when the variance of arrival times of the echoes in a gather is sufficiently large (such that the echo arrivals in the gather do not coincide). However, statistical methods have limitations when the echo arrivals do not follow a known distribution as statistical methods of the first-order, and even more elaborate statistical methods, are insufficient to address the challenge.

SUMMARY

Described herein are systems, methods and devices for automatically characterizing one or more echoes contained in an ultrasonic signal. The ultrasonic signal can be generated with an ultrasonic transducer and reflected from a formation before being recorded by the ultrasonic transducer. Optionally, the systems, methods and devices can operate on a single ultrasonic trace to automatically locate and gate an echo embedded in the noisy ultrasonic signal. According to the implementations described herein, it is possible to construct more accurate initial guesses of one or more echo parameters, which improves the performance and robustness of an inversion algorithm (e.g., the space alternating generalized expectation (SAGE) maximization algorithm) used to optimize the echo parameters. The echo parameters obtained by inversion can then be used to generate an image, for example, an image of the formation from which the ultrasonic signal is reflected.

An example method for automatically characterizing an echo contained in an ultrasonic signal generated with an ultrasonic transducer can include receiving data corresponding to the ultrasonic signal with the ultrasonic transducer, calculating an energy ratio of the ultrasonic signal and localizing the echo contained in the ultrasonic signal using the energy ratio. The method can also include windowing a portion of the ultrasonic signal around the localized echo and calculating a Fast Fourier Transform (FFT) and a Hilbert envelop of the windowed portion of the ultrasonic signal. In addition, the method can include estimating M echo parameter vectors from the FFT and the Hilbert envelope of the windowed portion of the ultrasonic signal, calculating M parametric echo models based on each of the M echo parameter vectors and iteratively minimizing a difference between the windowed portion of the ultrasonic signal and a sum of the M parametric echo models. Each of the M parameter vectors can include a plurality of echo parameters.

Optionally, the energy ratio of the ultrasonic signal can be calculated and the echo contained in the ultrasonic signal can be localized using the energy ratio by calculating an energy ratio function of the ultrasonic signal, where the energy ratio function is $$E_x = a_1 \left( \frac{\sum_{i=x+1}^{x+L} E_i}{\sum_{i=x-L}^{x-1} E_i} \right) / (1 + a_2 E_{total}),$$

and identifying a maximum value of the energy ratio function of the ultrasonic signal. The maximum value can correspond to an approximate location of the echo contained in the ultrasonic signal. In the energy ratio function above, $E_x$ is energy at a given data point, $a_1$ and $a_2$ are energy adjustment factors, L is a window length, $$\sum_{i=x+1}^{x+L} E_i$$

is signal energy, $$\sum_{i=x-L}^{x-1} E_i$$

is noise energy and $E_{total}$ is total energy.

Alternatively or additionally, the energy ratio function of the ultrasonic signal can be calculated by reversing the data corresponding to the ultrasonic signal from head-to-tail to tail-to-head, calculating the energy ratio function of the reversed ultrasonic signal and identifying a maximum value of the energy ratio function of the reversed ultrasonic signal. The maximum value of the energy ratio function of the ultrasonic signal can correspond to a left side of a first echo contained in the ultrasonic signal, and the maximum value of the energy ratio function of the reversed ultrasonic signal can correspond to a right side of the first echo contained in the ultrasonic signal.

Alternatively or additionally, the energy ratio function of the ultrasonic signal can be calculated by cropping the data corresponding to the ultrasonic signal, calculating the energy ratio function of the cropped ultrasonic signal and identifying a maximum value of the energy ratio function of the cropped ultrasonic signal. The maximum value of the energy ratio function of the ultrasonic signal can correspond to a left side of a first echo contained in the ultrasonic signal, and the maximum value of the energy ratio function of the cropped ultrasonic signal can correspond to a left side of a second echo contained in the ultrasonic signal.

Optionally, the window length (L) can be approximately equal to s $$\frac{f_s}{f_c},$$

where s is a tuning coefficient, $f_c$ is a center frequency of the ultrasonic signal and $f_s$ is a sampling frequency.

Alternatively or additionally, a portion of the ultrasonic signal around the localized echo can optionally be windowed by applying a half-Hanning taper to data corresponding to one or more sides of the ultrasonic signal outside of the windowed portion of the ultrasonic signal.

Optionally, a difference between the windowed portion of the ultrasonic signal and a sum of the M parametric echo models can be iteratively minimized by performing at least one of a Gauss-Newton (GN) optimization, a genetic algorithm (GA) and an evolutionary optimization meta-heuristic approach.

Alternatively or additionally, the M parametric echo models can be calculated by calculating M parametric echo models based on each of the M echo parameter vectors and the windowed portion of the ultrasonic signal. Further, a difference between the windowed portion of the ultrasonic signal and a sum of the M parametric echo models can be iteratively minimized by determining the plurality of echo parameters for each of the M echo parameter vectors based on each of the M parametric echo models, updating the M echo parameter vectors, determining if the updated M echo parameter vectors converge with the M echo parameter vectors and if convergence is not achieved, calculating M parametric echo models based on each of the updated M echo parameter vectors and the windowed portion of the ultrasonic signal. The process for iteratively minimizing a difference between the windowed portion of the ultrasonic signal and a sum of the M parametric echo models can be repeated until convergence is achieved.

In addition, the method can optionally further include filtering the data corresponding to the ultrasonic signal to remove at least one baseline component of the ultrasonic signal.

Alternatively or additionally, the plurality of echo parameters can include at least one of a bandwidth factor ($\alpha$), an arrival time ($\tau$), a center frequency ($f_c$), a phase ($\phi$) and an amplitude ($\beta$). Optionally, the method can further include generating an image using the plurality of echo parameters.

An example system for automatically characterizing an echo contained in an ultrasonic signal can include an ultrasonic transducer configured to generate and receive an ultrasonic signal and a control unit including at least one processor and a memory. The ultrasonic transducer can optionally be located in a borehole. The control unit can be configured to receive data corresponding to the ultrasonic signal from the ultrasonic transducer, calculate an energy ratio of the ultrasonic signal and localize the echo contained in the ultrasonic signal using the energy ratio. The control unit can be further configured to window a portion of the ultrasonic signal around the localized echo and calculate a FFT and a Hilbert envelop of the windowed portion of the ultrasonic signal. In addition, the control unit can be further configured to estimate M echo parameters from the FFT and the Hilbert envelope of the windowed portion of the ultrasonic signal, calculate M parametric echo models based on each of the M echo parameter vectors and iteratively minimize a difference between the windowed portion of the ultrasonic signal and a sum of the M parametric echo models. Each of the M parameter vectors can include a plurality of echo parameters.

It should be understood that the above-described subject matter may also be implemented as a computer-controlled apparatus, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIGS. 4A-4E are graphs illustrating an example pulse-echo waveform parameterized using a model order of two (e.g., M=2);

FIGS. 8-10 are graphs illustrating a plurality of gating techniques according to implementations discussed herein;

FIGS. 13A-13G illustrate the results of ultrasonic echo parameterization using three Gaussian echoes on a single trace of example borehole data;

FIG. 14 is a graph illustrating a magnified view of the parameterization of FIGS. 13A-13F inside the windowed portion of the ultrasonic signal;

FIGS. 18A-18F are graphs illustrating the decomposition of an ultrasonic signal;

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. While implementations will be described for automatically characterizing an echo in an ultrasonic signal generated and detected by an ultrasonic transducer arranged in a fluid-filled borehole, it will become evident to those skilled in the art that the implementations are not limited thereto but are applicable for characterizing an echo in ultrasonic signals in other environments.

Ultrasonic Echo Processing

Figure 1:
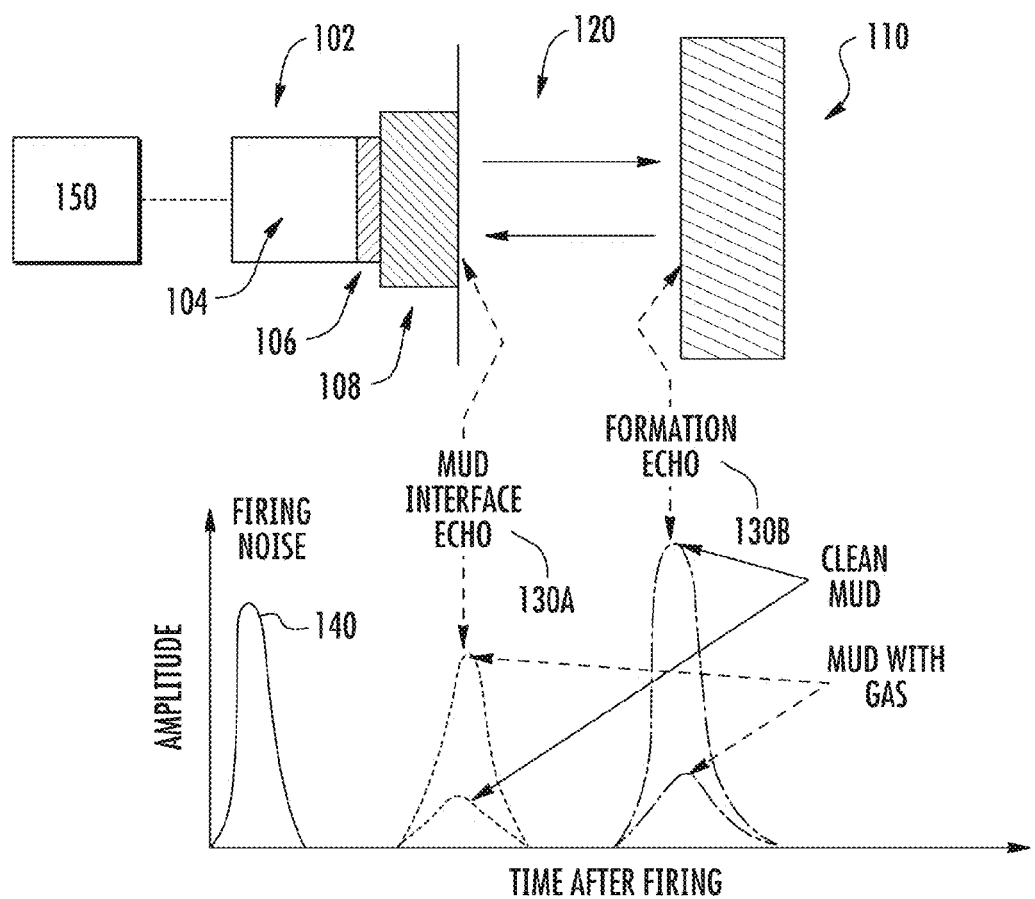
FIG. 1 is a diagram illustrating a pulse-echo configuration of an ultrasonic transducer with a corresponding signal.

Referring now to FIG. 1, a diagram illustrating a pulse-echo configuration of an ultrasonic transducer 102 with a corresponding signal is shown. The ultrasonic transducer 102 can optionally be an acoustic tool designed for deployment in a fluid-filled borehole. The acoustic tool can optionally include a plurality of ultrasonic transducers, e.g., the acoustic tool can optionally be an acoustic array. The borehole can be drilled in a formation 110 containing a desirable fluid deposit such as oil or gas. The ultrasonic transducer 102 can therefore be used to obtain information about the formation 110 as discussed in detail below.

The ultrasonic transducer 102 can include a backing 104, a ceramic element 106 and a delay line 108. The ceramic element 106 can include one or more piezoelectric elements. When a voltage pulse is applied to a piezoelectric element, the piezoelectric element transmits a pressure wave (e.g., an ultrasonic wave). When a reflected pressure wave is intercepted by a piezoelectric element, the piezoelectric element converts the intercepted pressure wave into a voltage pulse. Additionally, the delay line 108 can optionally be configured to control the delay time of the ultrasonic pulse transmitted or received by the ceramic element 106, minimize ultrasonic pulse scattering, provide impedance matching between the transmitter and receiver, etc. Ultrasonic transducers are well known in the art and are therefore not discussed in further detail below.

Optionally, the ultrasonic transducer 102 can operate in a pulse-echo or reflection mode, where the ultrasonic transducer 102 both emits an ultrasonic pulse and receives the reflected ultrasonic pulse. For example, the emitted ultrasonic pulse can travel through a fluid 120 (e.g., water or mud) and can reflect off of the formation 110 before returning back to the ultrasonic transducer 102. The reflected signal can be captured as a measured electrical voltage. Such a measurement is referred to as a pulse-echo. The pulse-echo 130A-B is shown in FIG. 1. It should be understood that the pulse-echo can be the result of reflection off of the mud interface (e.g., a mud interface echo 130A) and/or the formation 110 (e.g., a formation echo 130B). Additionally, the amplitude of the pulse-echo 130 A-B is affected by the amount of gas present in the mud as shown in FIG. 1. Further, it should also be understood that the ultrasonic transducer 102 can measure the firing noise 140.

Pulse-echo measurements can be used for imaging purposes, e.g., imaging the formation 110. The basis for creating an image comes from two measured attributes of the acquired pulse-echo waveform—travel time and amplitude. It should be understood that travel time is a length of time between excitation (or firing) of the ultrasonic transducer 102 and reception of the reflected ultrasonic echo. Travel time can be directly correlated to the size and shape of the borehole. It should be understood that amplitude of the reflected ultrasonic pulse (e.g., the pulse-echo waveform) can be used to characterize the acoustic impedance of the fluid 120, as well as the formation 110, including fractures, texture, vugs, etc. Optionally, to extract the above attributes, a Hilbert envelope of the pulse-echo wave form can be calculated. The amplitude of the maximum peak of the Hilbert envelope and the location at which the maximum peak occurs correspond respectively to the amplitude and travel time of the main echo in the pulse-echo waveform. As discussed in detail below, the basic principle of extracting the above attributes is complicated in actual practice.

The ultrasonic transducer 102 can be operably connected with a control unit 150. It should be understood that the control unit 150 can optionally be located above, on and/or below the surface of the formation 110. Alternatively or additionally, the control unit 150 can be integrated with the ultrasonic transducer 102 and arranged in the borehole. The ultrasonic transducer 102 and the control unit 150 can be connected by a communication link. This disclosure contemplates the communication link is any suitable communication link. For example, a communication link may be implemented by any medium that facilitates data exchange between the ultrasonic transducer 102 and the control unit 150 including, but not limited to, wired, wireless and optical links. The control unit 150 can optionally be configured to control the ultrasonic transducer 102, as well as receive, process and store acoustic data (e.g., the acoustic data detected, collected, recorded, etc. by the ultrasonic transducer 102). In its most basic configuration, the control unit 150 typically includes at least one processing unit and system memory. Depending on the exact configuration and type of control unit 150, system memory may be volatile (such as random access memory (RAM)), non-volatile (such as read-only memory (ROM), flash memory, etc.), or some combination of the two. The processing unit can be a standard programmable processor that performs arithmetic and logic operations necessary for operation of the control unit 150.

For example, the processing unit can be configured to execute program code encoded in tangible, computer-readable media. Computer-readable media refers to any media that is capable of providing data that causes the control unit 150 (i.e., a machine) to operate in a particular fashion. Various computer-readable media may be utilized to provide instructions to the processing unit for execution. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In addition, the control unit 150 can have additional features/functionality. For example, the control unit 150 may include additional storage such as removable storage and non-removable storage including, but not limited to, magnetic or optical disks or tapes. The control unit 150 may also contain network connection(s) that allow the device to communicate with other devices. The control unit 150 may also have input device(s) such as a keyboard, mouse, touch screen, etc. Output device(s) such as a display, speakers, printer, etc. may also be included. The additional devices may be connected to the bus in order to facilitate communication of data among the components of the control unit 150. All these devices are well known in the art and need not be discussed at length here.

Figure 2A:
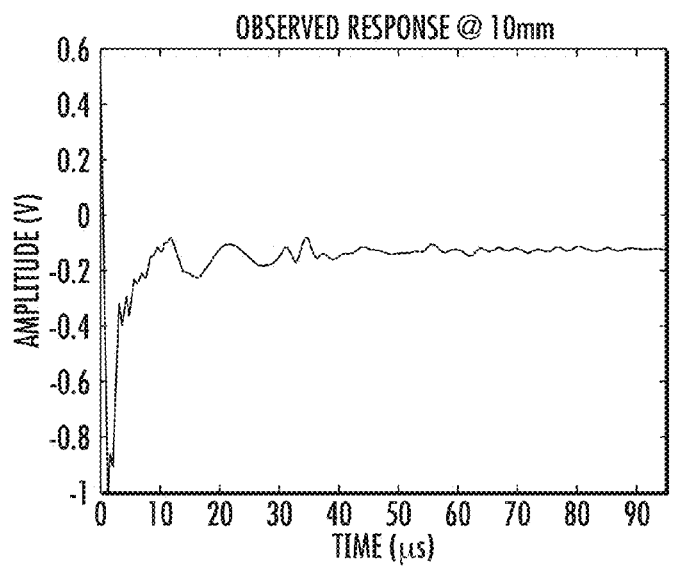
FIGS. 2A-2C are graphs illustrating example ultrasonic signals received at an ultrasonic transducer.
Figure 2B:
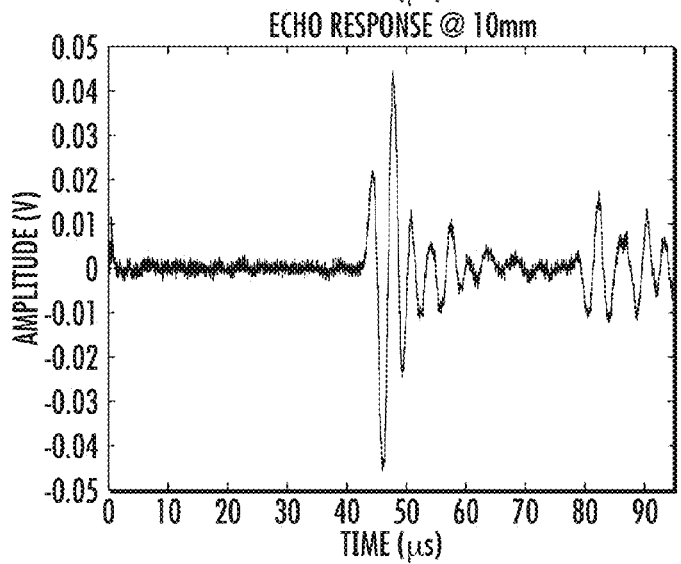
Figure 2C:
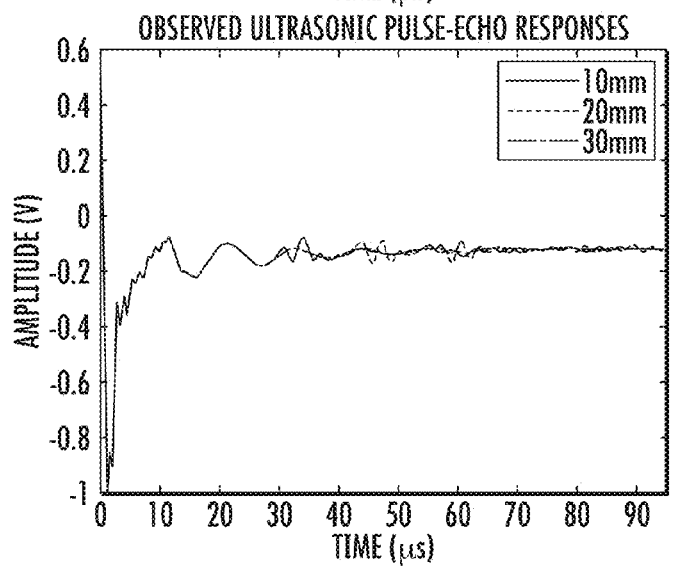

Referring now to FIGS. 2A-2C, graphs illustrating example ultrasonic signals received at an ultrasonic transducer are shown. The ultrasonic signal is composed of two components—a baseline and the measured pulse-echo waveform (e.g., the pulse-echo response of the reflector or the pulse-echo response). The baseline includes the transducer excitation pulse and response as well as noise, for example. In FIGS. 2A-2C, the ultrasonic signals are composed of three distinct regions: the ultrasonic transducer excitation pulse occurring from approximately 0 µs to 10 µs, followed by the ultrasonic transducer response (e.g., exhibiting a ringing which tapers down from 10 µs onward), and finally, the pulse-echo response of the reflector at approximately 30 µs. FIG. 2A is a graph illustrating the ultrasonic signal produced by a reflector positioned approximately 10 mm from the ultrasonic transducer. FIG. 2B is a graph illustrating the pulse-echo hidden in the baseline of FIG. 2A. FIG. 2C is a graph illustrating the ultrasonic signals produced by reflectors positioned approximately 10 mm, 20 mm and 30 mm, respectively, from the ultrasonic transducer.

The amplitude and arrival time of the pulse-echo response of the reflector (e.g., the pulse-echo response) can be extracted by means of Hilbert envelope. The time and amplitude of the maximum peak of the Hilbert envelope can be used as the two attributes of the pulse-echo response for imaging purposes. It should be understood that there is a certain degree of error that exists in the reading of the two attributes from the Hilbert envelope due to the ringing that is inherent to the ultrasonic transducer. The severity of this error depends on the arrival time of the reflection echo in relation to the ringing of the ultrasonic transducer, where earlier arrivals can be obscured more by the initial ringing of the ultrasonic transducer. In light of the amplitude and arrival time attribute errors introduced by the ringing of the ultrasonic transducer, it is optionally desirable to remove this ringing baseline from the acquired ultrasonic signal. All traces in a particular gather will be contaminated with such a ringing of the transducer. To address the issues stemming from this ringing baseline problem, a parameterization technique, which is discussed in detail below, can be used.

Parameterization

Extraction of the exact amplitude and arrival time attributes is a matter of detecting the first peak in the pulse-echo response and the corresponding time at which the first peak occurs. When the signal-to-noise ratio (SNR) is sufficient, extracting the pulse-echo response attributes can be a trivial matter, for example, by means of applying the Hilbert envelope. However, in cases when sufficient SNR does not exist (e.g., in the presence of a strong ringing), the pulse-echo response amplitude and arrival time attributes can contain errors.

As discussed above, to remove the baseline from an ultrasonic signal to facilitate extraction of the pulse-echo response from the ultrasonic signal, statistical techniques such as averaging (or stacking) have been used to produce an estimate of the baseline that is contaminating the pulse-echo response. Statistical techniques can work well to estimate the baseline when the range of arrival times of the echoes in the gather is sufficiently large that the echoes do not overlap with each other. For any sort of statistical technique to be successful, there should be a portion of one trace somewhere in the gather that does not contain any baseline, otherwise the portion of the true signal will be added to the baseline estimate. Essentially, the problem manifests itself when the echo arrivals do not belong to a known distribution. In the case of logging-while-drilling tools (LWD) tools, the nominal stand-off range is difficult to control and typically varies between 0.4 inches and 1.00 inch. Due to this narrow stand-off range, it can be difficult to effectively remove the baseline using statistical techniques.

Parameterization is an alternative technique that can be used to remove the pulse-echo response from the ultrasonic signal. Through parameterization, the information contained in multiple traces is not relied upon, and instead, only a single trace of ultrasonic data can optionally be used. Additionally, it is possible to quantify and extract key features of the pulse-echo response (e.g., arrival time, amplitude, phase, center frequency, and bandwidth) in the ultrasonic data directly in the time domain. This is true even under conditions of noise and overlap. It is also possible to use modular models custom-tailored to the pulse-echo response that are being sought. By doing so, a particular ultrasonic trace can be decomposed into the pulse-echo response and the residual, which contains the baseline, out of a single trace. Thus, the hindrance of low stand-off variances is by-passed. Further, the volume of data that is to be recorded can be reduced. Parameterization can be seen as a form of lossy data compression. In the down-hole environment, where memory size is a scarce commodity, reducing the volume of recorded data enables the possibility of recording data for a longer amount of time. For instance, instead of recording a signal of trace length 256, through parameterization, the pulse-echo response can be represented through 5 parameters.

The Gaussian Echo Model

The Gaussian echo model can be chosen because it is well suited for characterizing ultrasonic signals. A single echo from a reflector can be represented by way of:

$$s(\theta;t) = \beta e^{-\alpha(t-\tau)^2} \cos(2\pi f_c)(t-\Sigma+(\phi) \tag{1}$$

$$\theta = [\alpha \tau f_c \phi \beta]$$

which embodies the form of a Gaussian-shaped envelope. The echo parameters are stored in a vector $\theta$, which is composed of five variables:

| | |
|---|---|
| $\alpha$ | bandwidth factor (MHz$^2$) |
| $\tau$ | arrival time (µs) |
| $f_c$ | center frequency (MHz) |
| $\phi$ | phase (rad) |
| $\beta$ | amplitude (V) |

Figure 3A:
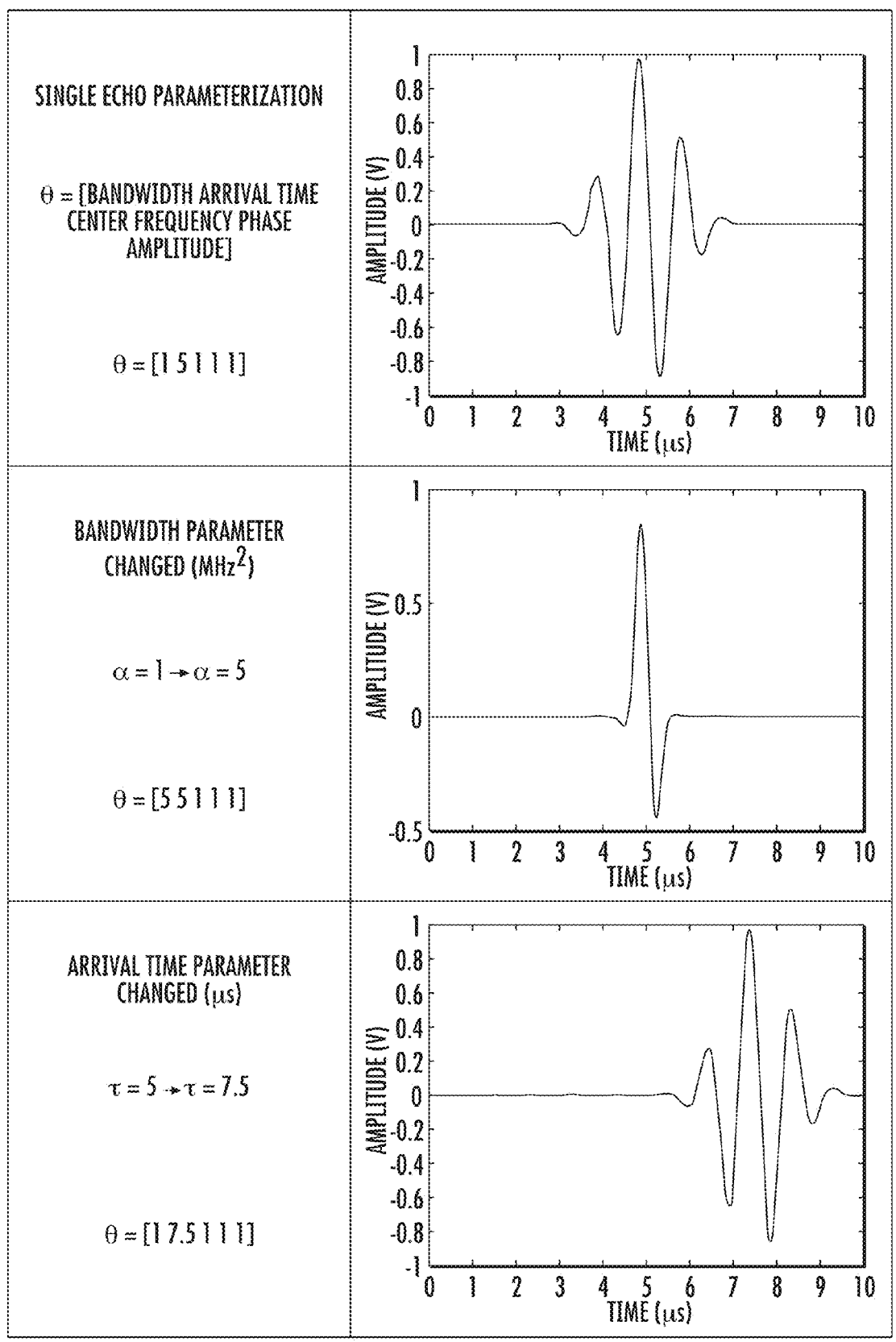
FIGS. 3A-3B are tables illustrating the effect of each parameter (e.g., bandwidth factor, arrival time, center frequency, phase and amplitude) on a parameterized waveform.
Figure 3B:
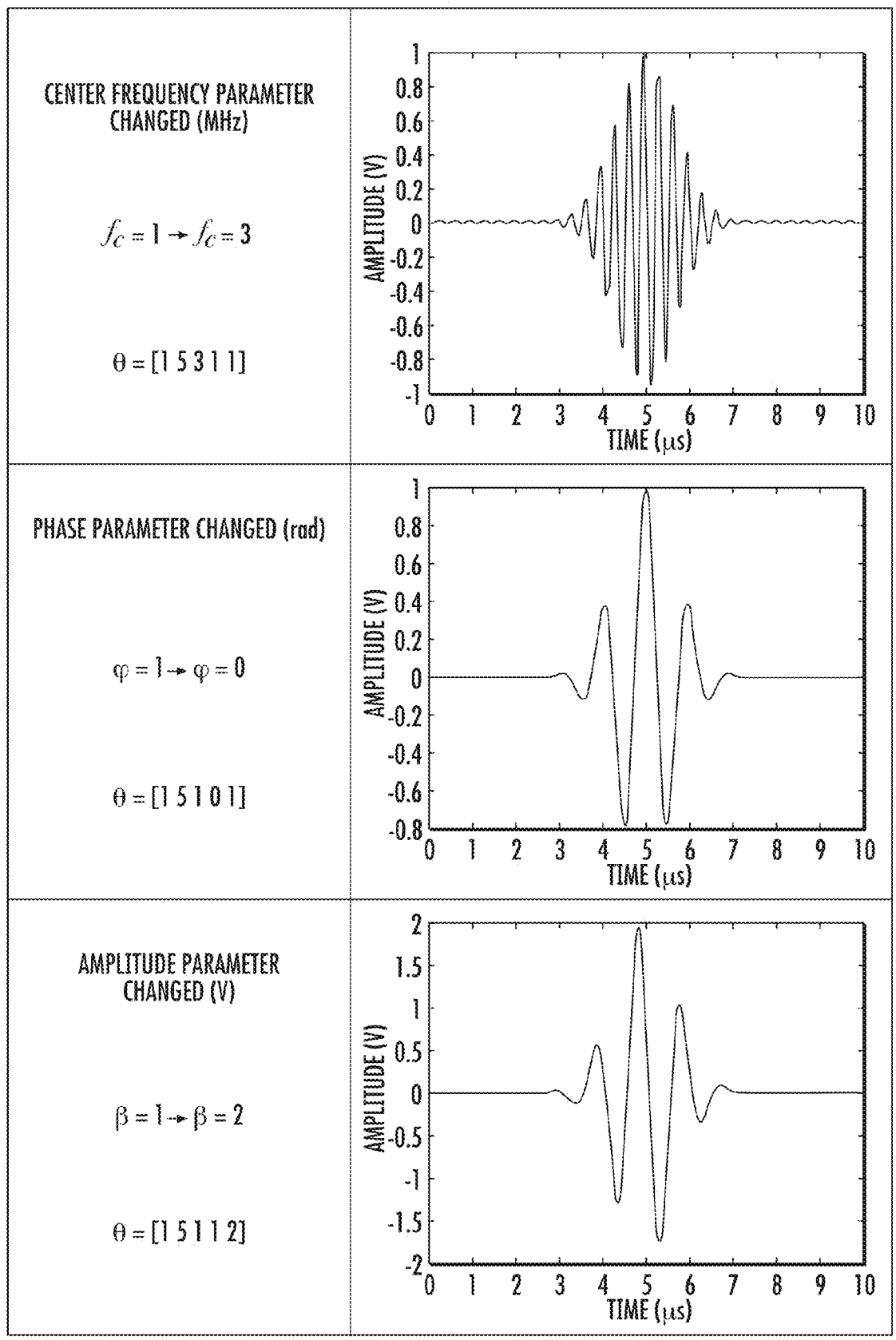

The values of the parameter vector θ directly correspond to the physical properties of the reflector. Arrival time τ relates to the distance from the reflector (e.g., the borehole wall). α, the bandwidth factor, is the duration of the echo in the time domain. $f_c$ is a product of the ultrasonic transducer's center frequency. Amplitude β and phase ϕ account for impedance and size and orientation (e.g., tilt) to the reflector. FIG. 3 is a table that illustrates the effect of each parameter on the parameterized waveform.

Observational Model of an Ultrasonic Echo

A Gaussian wavelet lends itself well to the modeling and approximation of ultrasonic signals. The observed model of a single ultrasonic echo including noise and other artifacts can be represented as:

$$x(t)=s(\theta;t)+v(t)=\beta e^{-\alpha(t-\tau)^2}\cos(2\pi f_c(t-\tau)+\phi)+v(t) \quad (2)$$

where s(θ; t) is the ultrasonic echo and v(t) account for noise and error (e.g., the component of the ultrasonic signal not encompassed in the parameterization).

The Gaussian echo model can be extended to approximate echoes of greater complexity through the principle of superposition. For example, the approximation of a pulse-echo, y(t), can become a sum of M superimposed Gaussian echoes as:

$$y(t)=\Sigma_{m=1}^{M} s(\theta_m;t)+v(t) \quad (3)$$

The parameter vector $\theta_m$ defines the shape and location of each individual echo. As in the case of a single echo parameterization, v(t) is the residual that includes noise and approximation error due to complexities that cannot be embodied in the model of a lower order.

Referring now to FIGS. 4A-4E, graphs illustrating an example pulse-echo waveform parameterized using a model order of two (e.g., M=2) are shown. Specifically, FIGS. 4A and 4B respectively illustrate the two individual Gaussian echoes 402 and 404 (e.g., the first arriving at 26.979 μs and the second at 32.0276 μs). The original pulse-echo waveform 406 (e.g., the ultrasonic signal) is illustrated in FIG. 4E. As discussed herein, the ultrasonic signal is the data recorded by the ultrasonic transducer. The summation of the two individual Gaussian echoes 402 and 404 produce the overall estimate of the arriving echo. This estimate (or reconstruction) 408 is shown relative to the original pulse-echo waveform 406 in FIG. 4D. In FIG. 4C, the difference between the reconstruction 408 the original pulse-echo waveform 406, which forms the remainder 410 (e.g., v(t)) is shown. The remainder 410 includes the second and third echoes, which have less value in parameterizing the pulse-echo response because these echoes contain limited information for imaging.

By parameterization, the ultrasonic signal (e.g., the original pulse-echo waveform 406 of FIG. 4E), which is approximately 5000 samples in length can be reduced to a parametric description using two Gaussian echo wavelets, each including 5 elements (i.e., 10 parameters total). The region where the first echo exists, which is the focal point of the parameterization, has been approximated with less than 2% error. Additionally, it is also worth noting the substantial reduction in the data volume that has been realized where the 10 parameter representation of the echo yields a 50-fold reduction in data volume in comparison to the original recording of the raw first echo waveform (500 samples). Table 1 below shows the estimated parameters for the two individual Gaussian echoes 402 and 404 of FIGS. 4A and 4B.

| ESTIMATED PARAMETERS | | | | | |
|---|---|---|---|---|---|
| | Bandwidth Factor (MHz²) | Arrival Time (μs) | Center Frequency (MHz) | Phase (rad) | Amplitude (V) |
| Echo #1 | 0.1338 | 26.9790 | 0.1839 | 3.6802 | 0.3987 |
| Echo #2 | 0.0321 | 32.0276 | 0.2034 | −11.5879 | 0.9999 |

Having introduced the fundamental parametric constructor (e.g., the Gaussian echo model) and how its implementation in the overall observational model of a pulse-echo waveform, determination of the optimal model parameters that best describe the waveform of the ultrasonic signal are discussed in detail below. To produce an estimate of the ultrasonic signal, a comparison can be made between the echoes described in the parameterization and the ultrasonic echo of interest in the waveform. The parametric estimation in Eqn. (1) above (i.e., s(θ; t)) changes are governed by the observations in the input signal x (e.g., the signal recorded at the ultrasonic transducer). The transformation from the parameter space to signal space is non-linear even though it is described by an empirical Gaussian echo model. Therefore, the inversion process is also non-linear. Additionally, fitting an empirical model to real data is obscured by noise and ringing, which complicates the estimation of parameters.

To address this non-linear parameter estimation problem, a Maximum Likelihood Estimation (MLE) framework is provided below. The MLE is found by minimizing an objective function comprised of the observed data x (e.g., the ultrasonic signal) and the current parametric signal model s(θ) as:

$$J(\theta)=(x-s(\theta))^T(x-s(\theta))=\|x-s(\theta)\|^2 \quad (4)$$

The goal is to minimize the difference between the observed data and the parametric estimate. In computing the objective function, it is evident that it is non-linear in the vector θ. Due to this, the optimization problem is established as an unconstrained non-linear least-squares (LS) problem because there is no constrained region on the parameter vector.

Algorithms to solve unconstrained LS problems operate in an iterative manner. To begin, an initial guess is made for the parameter vector, and with each iteration, the parameter vector undergoes improvements to minimize the objective function. When the objective function reaches a minimum, the optimal parameters have been found (e.g., a global minimum). It should be understood that local minima can exist and depending on the initial guess, the algorithm may get trapped in one of these local minima, resulting in a suboptimal solution. Therefore, it is desirable to determine the initial parameters to ensure optimal convergence.

Gauss-Newton Optimization

The Gauss-Newton (GN) optimization can optionally be used to solve the aforementioned unconstrained LS problem. With each iteration of the GN process, the parameter vector θ is updated, resulting in an improvement in the objective function. This disclosure contemplates using other techniques to solve the unconstrained LS problem, including but not limited to a genetic algorithm (GA), an evolutionary optimization meta-heuristic approach or a particle swarm optimization (PSO).

The GN update formula can be written as:

$$\theta^{k+1}=\theta^k+(H^T(\theta^k)H(\theta^{(k)}))^{-1}H^T(\theta^{(k)})(x-s(\theta^{(k)})) \quad (5)$$

where $\theta^k$ is the current parameter estimate and H(θ) is the gradient of the model with respect to the parameter vectors

[α τ $f_c$ φ β]. (x−s($\theta^{(k)}$)) is the difference between the observed signal and the current parametric reconstruction.

The vector H(θ) is comprised of partial derivatives of each parameter. These partial derivatives are expensive to compute, which is an important consideration because to update them, the partial derivatives are recomputed with every iteration. With this in mind, to speed up computation, the analytical gradients of the Gaussian echo can be utilized. The gradient matrix is written as:

$$H(\theta) = \left[ \frac{\delta s}{\delta \alpha} \frac{\delta s}{\delta \tau} \frac{\partial s}{\partial f_c} \frac{\partial s}{\partial \varphi} \frac{\delta s}{\delta \beta} \right] \quad (6)$$

$$\frac{\delta s(t; \theta)}{\delta \alpha} = -\beta(t - \tau) 2 f(t; \theta) \quad (7)$$

$$\frac{\delta s(t; \theta)}{\delta \tau} = 2\alpha\beta(t - \tau) f(t; \theta) + 2\pi f_c \beta g(t; \theta) \quad (8)$$

$$\frac{\delta s(t; \theta)}{\delta f_c} = -2\pi\beta(t - \tau) g(t; \theta) \quad (9)$$

$$\frac{\delta s(t; \theta)}{\delta \varphi} = -\beta g(t; \theta) \quad (10)$$

$$\frac{\delta s(t; \theta)}{\delta \beta} = f(t; \theta) \quad (11)$$

To further reduce computational complexity, the inverse of the gradient matrix $(H^T(\theta^k) H(\theta^{(k)}))^{-1}$ can be computed:

$$(H^T(\theta^k) H(\theta^{(k)}))^{-1} = \begin{bmatrix} \frac{3}{16\alpha^2} & 0 & 0 & 0 & \frac{-1}{4\alpha\beta} \\ 0 & \alpha + (2\pi f_c)^2 & 0 & -2\pi f_c & 0 \\ 0 & 0 & \frac{\pi}{\alpha} & 0 & 0 \\ 0 & -2\pi f_c & 0 & 1 & 0 \\ \frac{-1}{4\alpha\beta} & 0 & 0 & 0 & \frac{1}{\beta^2} \end{bmatrix} \quad (12)$$

The inversion algorithm can include the following steps:

Step 1: Begin with an initial guess for the parameter vector θ.

Step 2: Compute the gradients H($\theta^k$) and the model s($\theta^k$).

Step 3: Iterate the parameter vector:

$$\theta^{k+1} = \theta^k + (H^T(\theta^k))^{-1} H^T(\theta^k)(x - s(\theta^k))$$

Step 4: Check the convergence criterion against a predetermined tolerance:

$\|\theta^{k+1} - \theta^k\| < \text{tol}$, where tol is the difference between two consecutive parameter iterations. It should be understood that as the parameter vector is iterated, improvements in each of the parameters included in the parameter vector become marginal. The tolerance is a measure of the marginal change between the new parameter vector estimate (e.g., $\theta^{k+1}$) and the previous parameter vector estimate (e.g., $\theta^k$). This disclosure contemplates that the difference can be calculated as an absolute change or as a percentage change between the new and previous parameter estimates. For example, the tolerance can optionally be set to tol=0.01, which ensures that the algorithm converges and that subsequent improvements are negligible. This disclosure contemplates setting the tolerance to other values. If convergence has been achieved, terminate otherwise go on to step 5.

Step 5: Set k→k+1 (and continue the iteration).

Parameter Initialization

In order to parameterize an ultrasonic signal, it is desirable to make an accurate initial guess of the initial parameter vector. As discussed above, an accurate initial guess can improve the chance of finding the optimal solution, as well as reduce the number of computations required to find it. To make an accurate initial guess, a multi-stage process of detrending or removing the baseline from the ultrasonic signal, localizing the echo within the ultrasonic signal and windowing the ultrasonic signal before parameterization is discussed in detail below. As discussed above, the ultrasonic signal can be a single trace.

Baseline Removal

Optionally, a baseline removal operation can be applied to the ultrasonic signal to make the first pulse in the echo easier to identify. There are two components that contribute to the baseline that can be removed. The first stems from the excitation pulse of the ultrasonic transducer. The second stems from the ultrasonic transducer experiencing a ring-down of the excited piezo-electric element, which takes some time to subside. In addition to the ringing of the piezo-electric element, there can also be some ringing from the front-face window that protects the element. When the echo arrival occurs very early (e.g., when the reflector is placed at a low stand-off), then the initial echo can arrive while the ultrasonic transducer is still ringing down. This ringing can be affected by heat and temperature and the relationship is non-linear. To remove the baseline, three techniques have been used, each technique operating on multiple traces to form the estimate for the baseline.

Stacking is a commonly used technique to improve the SNR in seismic data. The principle behind stacking is to form an estimate of the baseline through computing an average of the observed traces. The components in the traces that do not change such as the firing response and the ringing of the ultrasonic transducer, for example, can form the baseline. Additionally, the components in the traces that do not change occur in every trace. Thus, when the traces in the gather are averaged, the components that change can be averaged out with the non-changing components to form the baseline estimate.

Another technique that can be used to estimate the baseline is singular value decomposition (SVD). SVD is a decomposition and ranking of the components of traces in a gather based on the level of variance that the traces exhibit between themselves. SVD can be used to exploit the main trend in the baseline that contaminates the traces in an ultrasonic gather. Because all of the traces in the gather share a common baseline, the baseline component has the highest rank. The other remaining contributing components such as the echoes and noise, for example, are typically weakly correlated and should manifest themselves in the SVD decomposition at a much lower rank compared to the baseline.

Using the top value of the SVD as the baseline works similarly to stacking with the same drawback, that is, if the echoes within the traces in the gather do not exhibit enough variance, the echoes can be key contributors to the baseline in the decomposition. In addition, SVD is significantly computationally more expensive than taking a simple mean of all of the traces within the gather.

Alternatively or additionally, subtraction is another technique that can be used to estimate the baseline. For example, if the ultrasonic echoes in two traces are sufficiently spaced apart (e.g., the lengths of the echoes do not coincide at the same time), then the baseline can be calculated by means of subtraction. For instance, two ultrasonic signals $S_1$ and $S_2$, which are both comprised of two sufficiently spaced echoes and a common baseline are provided below:

$$S_1 = E_1 + B \quad (13)$$

$$S_2 = E_2 + B \quad (14)$$

$$S_1 - S_2 = E_1 - E_2 \quad (15)$$

Subtracting both ultrasonic signals from one another can yield a trace that is composed of exactly two echoes $E_1$ and $E_2$, free of any baseline. It should be understood that the requirement that the echoes do not interfere with one another due to overlap is important. If the echoes overlap, it is possible to have an adverse effect on the overall amplitude of one or both of the echoes due to constructive or destructive interference. After performing the subtraction, the echoes can be extracted by the application of two gates to the ultrasonic signals and subtracting the echoes from their respective trace. Gating of ultrasonic signals is discussed in detail below. The result provides an approximation of the baseline, which can be used to de-noise the ultrasonic signals in the gather.

Echo Localization Using an Energy Ratio Technique

After optionally pre-processing the ultrasonic signal by detrending and removing the baseline components, the region within the trace that contains the first echo can be identified (or localized). The motivation behind locating the region in which the first echo is hidden is two-fold. First, localizing the first echo facilities a reduction in overall data volume. Additionally, localizing the first echo improves accuracy because parameterization efforts can be focused in a much tighter region (e.g., a narrower search space).

One technique for localizing the first echo is by way of calculating the energy ratio of the trace. Using the energy ratio function, the energy at a given point $E_x$ is calculated using the following formula:

$$E_x = a_1 \left( \frac{\sum_{i=x+1}^{x+L} E_i}{\sum_{i=x-L}^{x-1} E_i} \right) / (1 + a_2 E_{total}) \quad (16)$$

where,

| $\alpha_1$ = energy adjustment factor 1 | $\Sigma_{i=x+1}^{x+L} E_i$ = signal energy |
| $\alpha_2$ = energy adjustment factor 2 | $\Sigma_{i=x-L}^{x-1} E_i$ = noise energy |
| L = window length | $E_{total}$ = total energy |

It should be understood that Eqn. (16) is provided only as one example of an energy ratio function and that one of ordinary skill in the art can calculate the energy ratio function of the trace in a different way.

A given point x can be windowed from the both the left and right sides of the trace using a window of length, L. The energy content in the left and right window is assumed to be noise and signal, respectively. The ratio is constructed by comparing the signal energy to the noise energy. Additionally, the cumulative sum of the energy that resides in the entire signal, $E_{total}$ can be computed computed. Adjustment factors $a_1$ and $a_2$ can be used to minimize the impacts of late arrivals on the estimation of the first motion estimate. The first break in the signal is indicated by the location of the maximum value of the energy ratio function.

Figure 5B:
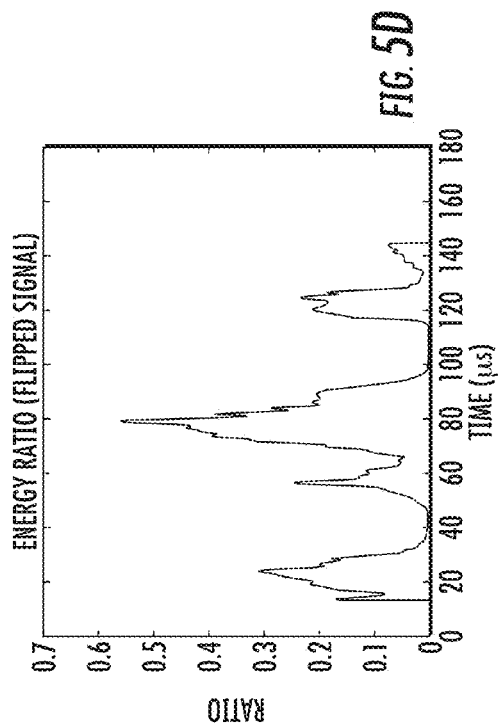
FIGS. 5A-5D are graphs illustrating an example pulse-echo signal recorded in a borehole and corresponding energy ratio calculations.
Figure 5A:
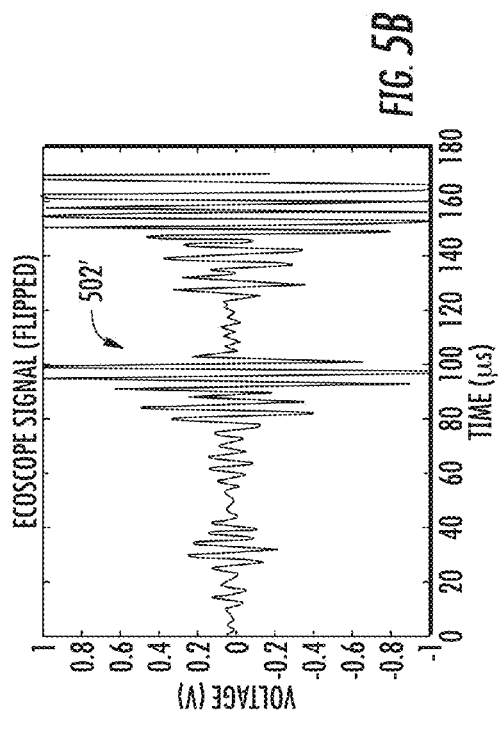
Figure 5D:
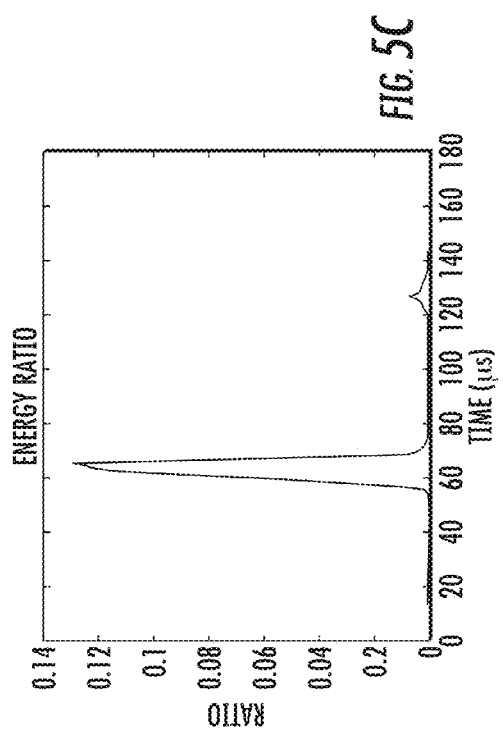
Figure 5C:
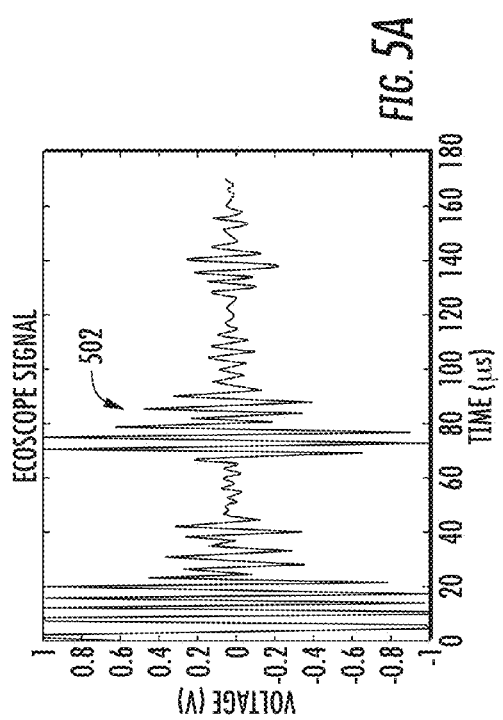

An example ultrasonic signal measured in a borehole is used to illustrate this localization technique. The example ultrasonic signal 502 is shown in FIG. 5A. The ultrasonic signal 502 includes 512 samples spanning from 0 μs to 170.66 μs (e.g., a 3 MHz sampling rate). The ultrasonic signal flipped from left to right 502' (i.e., the flipped ultrasonic signal) is shown in FIG. 5B. In other words, the ultrasonic signal is reversed from head-to-tail to tail-to-head. For example, in FIG. 5A, samples 0-511 are arranged from left to right. On the other hand, in FIG. 5B, samples 0-511 are arranged from right to left. The energy ratio of the ultrasonic signal 502 and the flipped ultrasonic signal 502' can be calculated using Eqn. (16) above with a window size of 40 (L=40) and energy adjustment factors $a_1$ and $a_2$ set at unity (i.e., 1). The energy ratio of the ultrasonic signal 502 is shown in FIG. 5C, and the energy ratio of the flipped ultrasonic signal 502' is shown in FIG. 5D.

Figure 6:
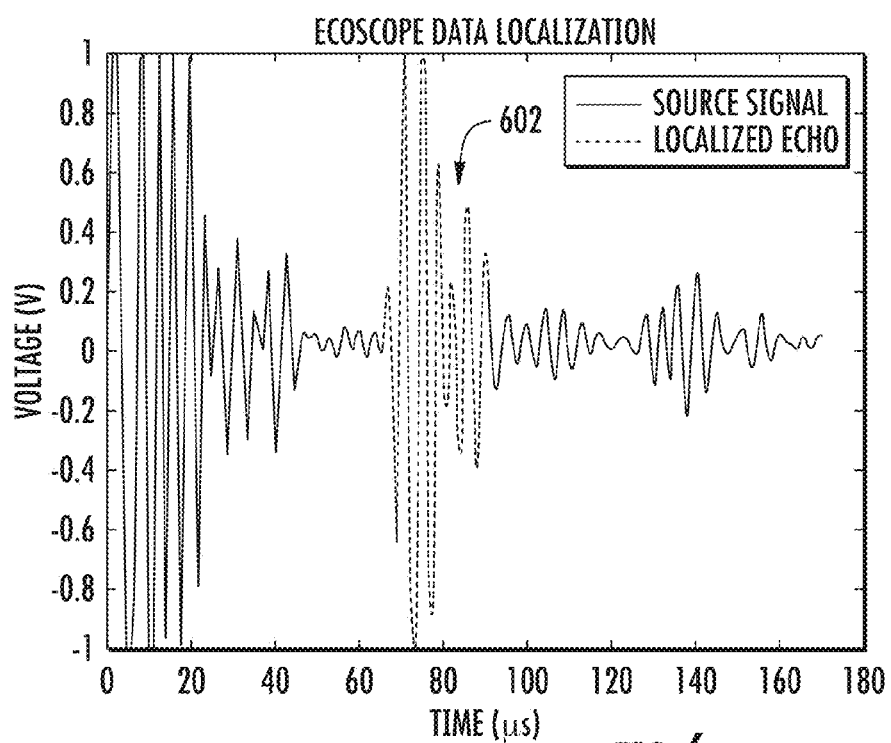
FIG. 6 is a graph illustrating the localized echo in the example pulse-echo signal shown in FIG. 5A.

The maximum values of the energy ratio functions indicate the breaks in the ultrasonic signal and the flipped ultrasonic signal. In other words, the energy ratio functions can be used to identify the left and right breaks of an echo in the ultrasonic signal. For example, the peak of the energy ratio of the ultrasonic signal in FIG. 5A occurs at t=66 μs. This localizes the arrival time of the echo from the left side (or the left break of the echo). The peak of the energy ratio of the flipped ultrasonic signal in FIG. 5B occurs at t=79.33 μs. This can be used to localize when the echo ends. For example, when the energy ratio of the flipped ultrasonic signal is flipped back from left to right (or reversed from tail-to-head to head-to-tail), the resulting time for the right break of the echo is t=170.66−79.33=91.33 μs. In such a way, the arriving echo has been located by the position of the left and right breaks (e.g., 66 μs and 91.33 μs). FIG. 6 shows the localized echo 602 of the ultrasonic signal 502 in FIG. 5A.

Window length, L, of the energy ratio function can determine the effectiveness of the energy ratio. Shorter window lengths produce energy ratio functions of higher resolution but with higher sensitivity to noise. On the other hand, longer window lengths are more robust against noise at the expense of offering lower resolving power. It is therefore desirable to select the window length with care such that it is insensitive to noise while still being able to correctly determine the first break in the ultrasonic signal.

Optionally, to automatically select the length of the energy ratio window, Eqn. (17) below can be used.

$$L = s \frac{f_s}{f_c} \quad (17)$$

Where $f_s$ and $f_c$ are the sampling rate and the central frequency of the ultrasonic signal, respectively. The multiplier, s, typically set to unity, is also included to tune the window length based on time between multiple echo arrivals (governed by the properties of the medium in which the pulse-echo response is recorded). According to Eqn. (17), the window length can be automatically and dynamically adjusted in response to different sampling frequencies as well as acquisition time intervals.

Figure 7A:
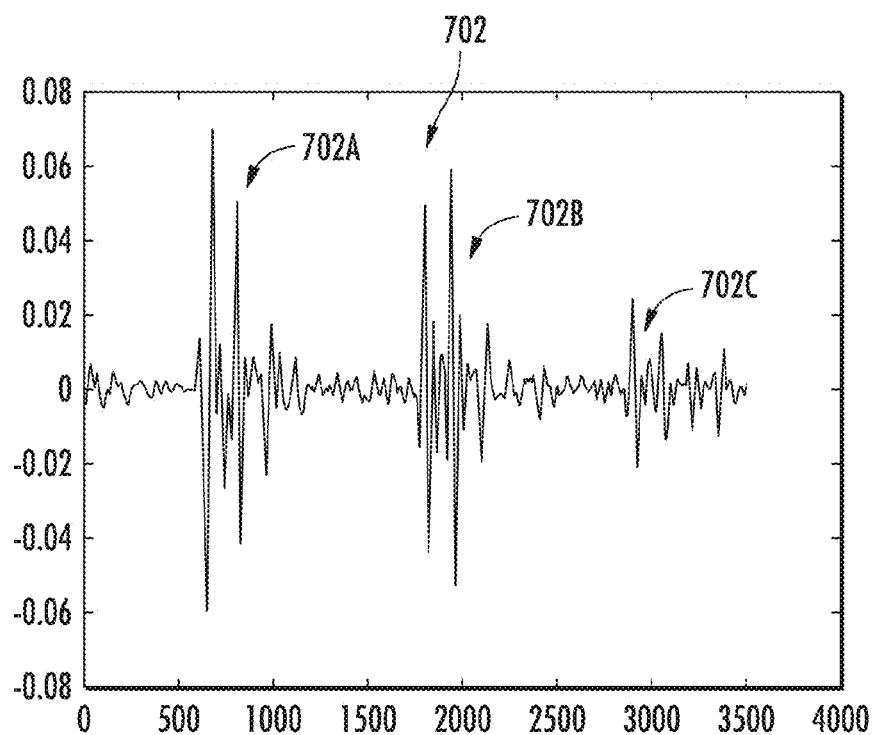
FIGS. 7A-7D are graphs illustrating the impact of using different window lengths for the energy ratio function.
Figure 7B:
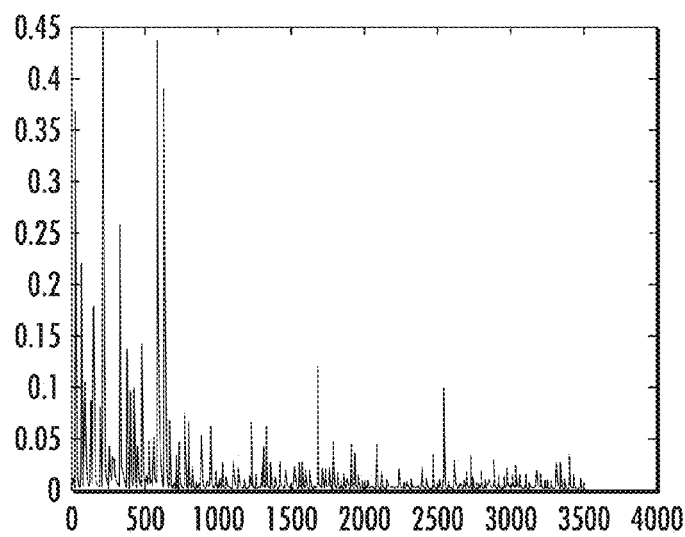
Figure 7C:
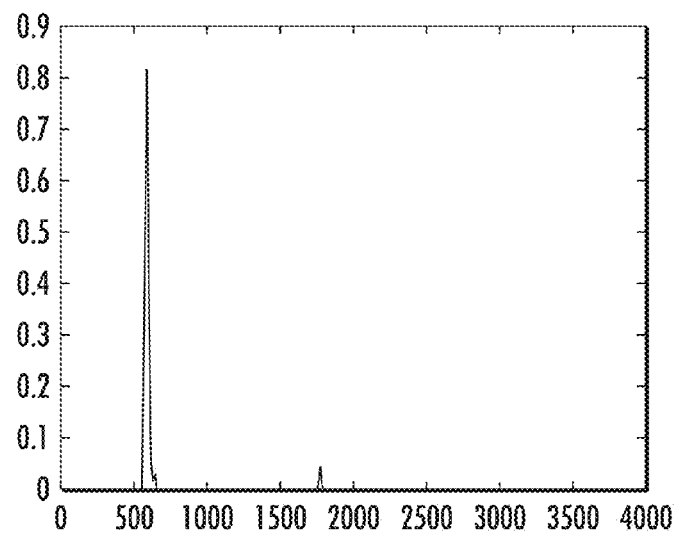
Figure 7D:
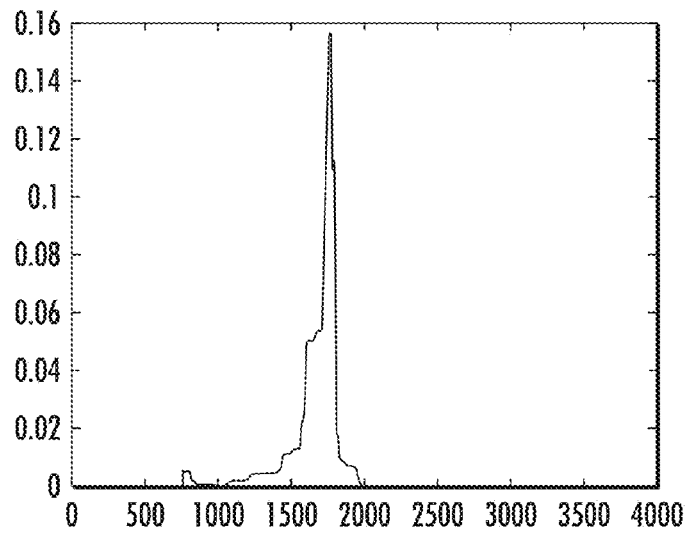

Referring now to FIGS. 7A-7D, graphs illustrating the impact of using different window lengths for the energy ratio function are shown. For example, FIG. 7A shows an example pulse-echo 702 recorded when a 250 kHz ultrasonic transducer is fired upon an aluminum reflector and a pulse-echo signal is acquired at 25 MHz. The recorded waveform exhibits three unique regions, e.g., first, second and third echoes 702A, 702B and 702C, respectively. As discussed above, the goal of echo localization is to correctly identify the first break in the pulse-echo signal. FIGS. 7B-7D show the results of applying the energy ratio function to the pulse-echo signal 702 in FIG. 7A using window lengths of L=7, 75, 750, respectively.

As shown in FIG. 7B, when the window length is too small (e.g., L=7), it is difficult to identify the first echo break because there is no easily distinguishable peak in the energy ratio function. Similarly, as shown in FIG. 7D, it is also difficult to identify the first echo break when the length of the window is too large (e.g., L=750). Specifically, the second echo break is detected when using a window length of 750 instead of the first echo break because the window length is larger than the location of the first echo (e.g., ~500 sample). As shown in FIG. 7C, when the window length is 75, the first echo break is correctly detected.

Echo Gating

Figure 9:
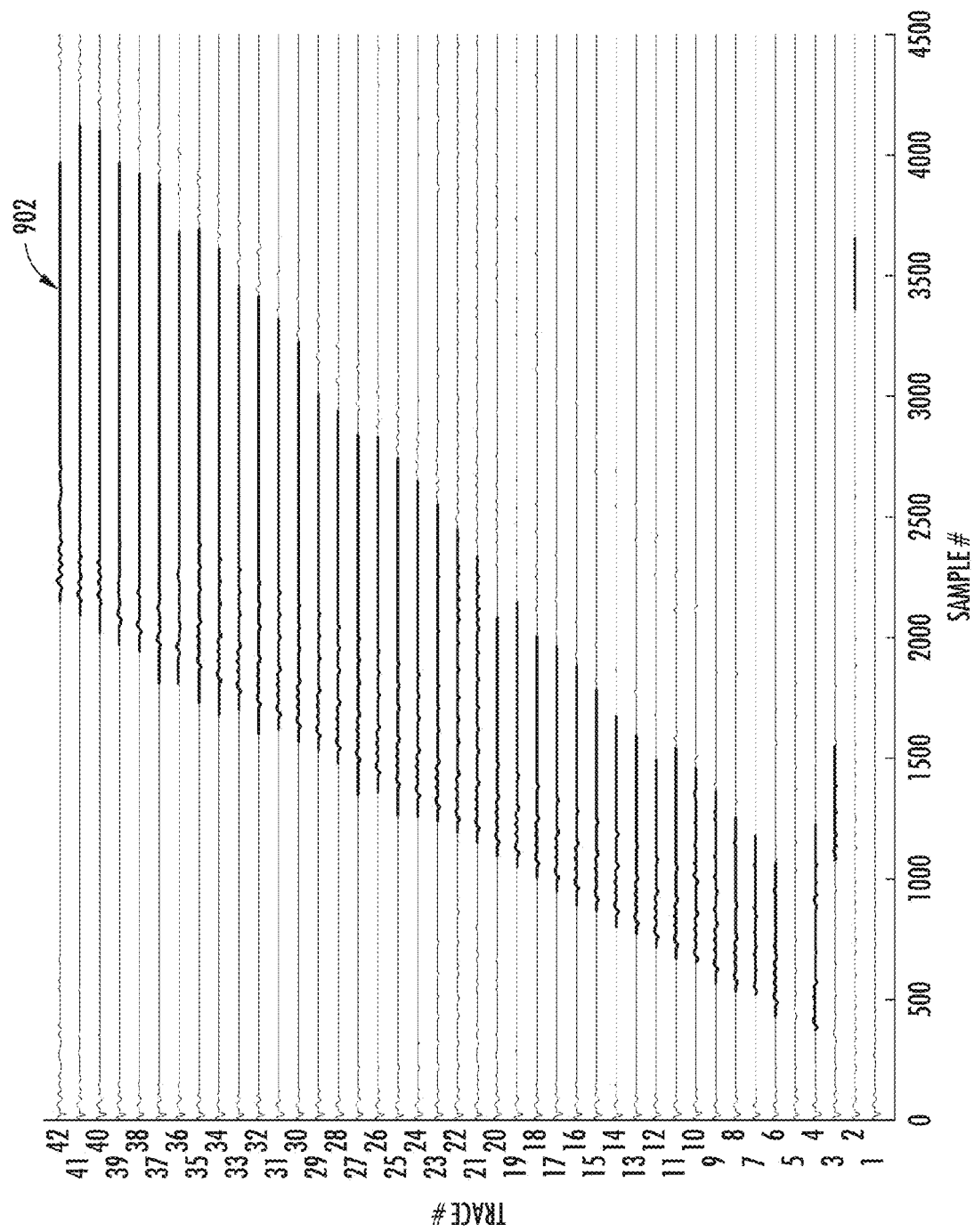
Figure 10:
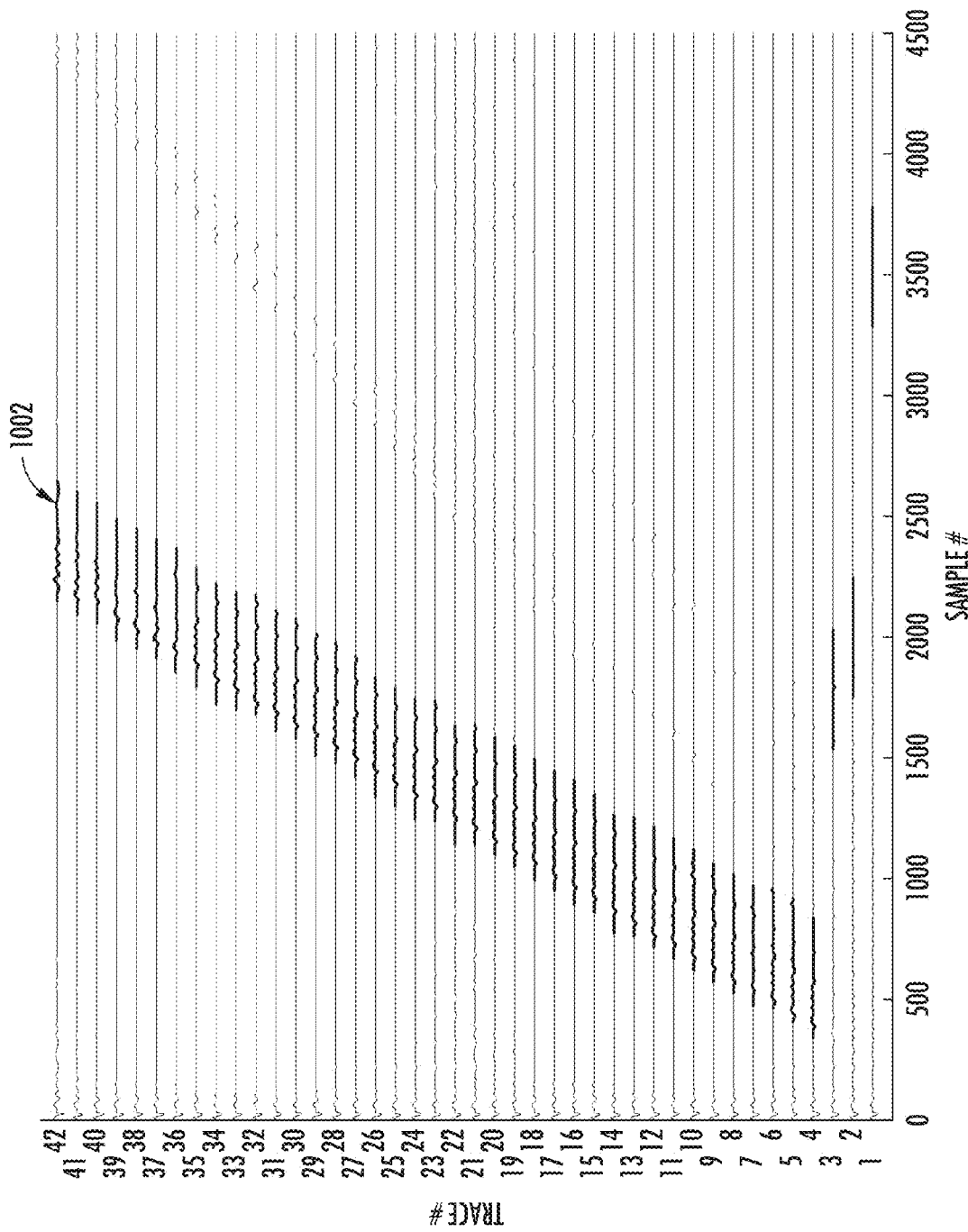

After finding the first echo break in the ultrasonic signal, there are several techniques that can be used to gate the recorded echo. Referring now to FIG. 8-10, graphs illustrating example gating techniques are shown. In FIG. 8, the energy ratio function is calculated from the left side of an ultrasonic signal. Then, the ultrasonic signal is flipped from left to right. In other words, the ultrasonic signal is reversed from head-to-tail to tail-to-head as discussed above with regard to FIGS. 5A-5B. Thereafter, the energy ratio function is calculated from the right side of the ultrasonic signal. As discussed above, the energy ratio function from the left side can be used to find the first echo break, e.g., the left break in the ultrasonic signal. Additionally, the energy ratio function from the right side can be used to find the right break in the ultrasonic signal. The position of the right break is then flipped from left to right so that it is properly positioned with respect to the left break. It should be understood that the left and right breaks can be used to gate the first echo in the ultrasonic signal. The gated portion 802 of each trace (e.g., the ultrasonic signal) is shaded in FIG. 8. This technique can be quite robust and can dynamically gate the first echo. It should be understood, however, that if a second echo with sufficient amplitude exists, the second echo can be detected as the right break. In this case, no data loss occurs but the gate is placed around the first break of the first echo and the tail end break of the second echo.

In FIG. 9, the energy ratio function is calculated from the left side of an ultrasonic signal. As discussed above, the energy ratio function from the left side can be used to find the first echo break, e.g., the left break in the ultrasonic signal. Then, the ultrasonic signal is cropped at the location of the first echo break. Thereafter, the energy ratio function is calculated from the left side of the cropped ultrasonic signal. The energy ratio function from the left side of the cropped signal can be used to find the next break in the ultrasonic signal, which corresponds to the second echo. It should be understood that the first and next breaks can be used to gate the first echo in the ultrasonic signal. The gated portion 902 of each trace (e.g., the ultrasonic signal) is shaded in FIG. 9. This technique can be more robust than gating from the left side of the ultrasonic signal and then gating from the right side of the flipped ultrasonic signal because there is typically some whitespace between the first and second echoes, which causes a large spike in the energy ratio function making it fairly easy to identify the second echo. It should be understood that when this technique is used there may be more redundant data (e.g., the whitespace between first and second echoes) included in the gating.

In FIG. 10, the energy ratio function is calculated from the left side of an ultrasonic signal. As discussed above, the energy ratio function from the left side can be used to find the first echo break, e.g., the left break in the ultrasonic signal. Then, a hard gate is set from the position of the left break. The length of the hard gate can be determined based on the expected duration of the first echo, which stems from the medium in which the pulse-echo travels. It should be understood that the first and hard breaks can be used to gate the first echo in the ultrasonic signal. The gated portion 1002 of each trace (e.g., the ultrasonic signal) is shaded in FIG. 10. This technique can be computationally the lightest of the techniques because only one energy ratio calculation is required. Additionally, the calculation of the first echo break from the left side of the ultrasonic signal is most robust compared to calculating the energy function from the right side of the flipped ultrasonic signal or again from the left side after cropping the ultrasonic signal.

In order to demonstrate each of the three gating techniques discussed above with regard to FIGS. 8-10, an ultrasonic transducer operating in water was used to collect data reflected from a simple reflector (e.g., aluminum) at incrementally varying distances from the reflector. For example, the stand-off range of the ultrasonic transducer from the reflector was adjusted in 1 mm increments from 0 mm up to 41 mm, (traces #1 to #42, respectively, where trace #1 corresponds to 0 mm of standoff) which moves the arriving echo further away from the firing response. The results of the demonstration are shown in FIGS. 8-10, and some general observations are noted below. As shown in FIGS. 8-10, gating from the left side of the ultrasonic signal is quite robust. For example, the first break in the signal is gated perfectly down to 4 mm as shown in each of FIGS. 8-10. Additionally, gating from the right side of the ultrasonic signal, for example after flipping the ultrasonic signal from left to right, is not as robust as gating from the left side of the ultrasonic signal. As discussed above, detecting the right break of the first echo in the ultrasonic signal can be challenging when there are subsequent echoes (e.g., second, third, etc.) arriving in the same acquisition window. For instance, if the peak pertaining to the second echo is stronger than the peak pertaining to the first echo, then when the energy ratio is applied, the gate will be applied to the tail end of the second echo instead of the trail end of the first echo. When this occurs, the first and second echoes are both gated as shown in trace numbers 21 to 37 as shown in FIG. 8. Additionally, as shown in FIG. 9, calculating the left break and then calculating the next left break works well down to approximately 10 mm. As discussed above, this generates trace lengths that are somewhat long because the gate encompasses the first echo and all the whitespace until the second echo. By applying a gating to the echo, it is also possible to exploit redundancy between echoes because they are all very similar when aligned to a common time reference. This benefit can lend itself well to the application of compression to further reduce the data volume within a gather.

Model Order Selection

The result of the inversion is a result of a summation of concurrently optimized Gaussian echoes. The model order can determine the effectiveness of the overall approximation of the ultrasonic echo at hand. For example, using a high model order enables the approximation of more complex waveforms but takes a longer time to converge at a solution. On the other hand, using a low model order is much less computationally intensive but can require more iterations to converge at a solution. Therefore, it is desirable to correctly choose the model order required to approximate the echo.

To maximize the effectiveness of the parameterization regardless of the model order that is chosen, the parameterization can be applied in a small localized region, for example by gating the echo portion of the ultrasonic signal. Then, the smaller, localized region (or gated portion) can be subject to analysis through the application of the Hilbert transform.

The Hilbert transform can be applied to the detrended and gated signal to reduce computational cost, and the Hilbert envelope can then be examined. Because the Gaussian echo is an empirical model selected to best approximate the ultrasonic echo, a single model order can be suitable for the echo and can correspond to a single peak in the ultrasonic signal. By examining the Hilbert envelope of the Gaussian echo, the number of critical peaks can be determined.

The number of peaks can be determined by means of a derivative-based peak finding function. A peak is indicated at the point in the derivative of the Hilbert envelope where the gradient changes from positive to negative. It should be understood that these points indicate the peaks in the function. In order to further refine the number of peaks determined, thresholding can be applied in terms of amplitude as well as the relative peaks from one another.

Then, the model order can optionally be selected as shown below:

$$M_{order} = \text{number of critical peaks detected in the window} + 1$$

The selected model order can be augmented by 1 to account for noise and the aberrations that may exist in the ultrasonic signal. The extra model order can be added to minimize noise since it is assumed that echoes can be obscured by noise and the GN optimization undergoes a minimization. If the extra model order is not added, the approximation of the echo inside the window attempts to account for the noise as well as the true echo within the window. By including the extra model order, the true echo can be fit to the models determined by the number of critical peaks in the window with the remaining model order taking up deviations from the non-empirical model.

Windowing and Initial Parameter Selection

After localizing the echo contained in the ultrasonic signal, the a portion of the ultrasonic signal around the localized echo can be windowed. As discussed above with reference to FIG. 6, the arriving echo was localized between the positions of the left and right breaks (e.g., 66 μs and 91.33 μs). Optionally, a half-Hanning filter can be applied to taper portions of the ultrasonic signal outside of the localized region (e.g., <66 μs and >91.33 μs). Alternatively or additionally, a window can be set around the localized echo that is 50% as large as the length localized echo. For example, the window can be set as follows:

$$\left[ 66 - \frac{(91.33 - 66)}{2}, 91.33 + \frac{(91.33 - 66)}{2} \right] = [52.67 \text{ μs}, 106 \text{ μs}].$$

Then, a half-Hanning taper can be applied to 5% to the regions outside of the window to bring the ends of the ultrasonic signal to zero. Thereafter, as discussed in detail below, the initial echo parameters can be selected. It should be understood that that applying a half-Hanning filter is provided only as one example windowing technique and that other windowing techniques can be used.

The echo parameters can then be estimated from the windowed portion of the ultrasonic signal. As discussed in detail below, estimates for amplitude and arrival time can be obtained by calculating a Hilbert envelop of the windowed portion of the ultrasonic signal and estimates for central frequency and bandwidth can be obtained by calculating a Fourier transform (e.g., using a FFT) of the windowed portion of the ultrasonic signal. This disclosure contemplates that other transforms known in the art can be applied to the windowed portion of the ultrasonic signal to facilitate obtaining the echo parameters. For example, a Windowed Fourier Transform and then a Hilbert transform can be applied to the windowed portion of the ultrasonic signal.

Amplitude and Arrival Time

The estimates for the initial amplitude and arrival time parameters, $\beta$ and $\tau$, can be set from the envelope of the windowed signal ($S_{win}$), which is calculated by taking the absolute value its Hilbert transform (H). The location and amplitude of the maximum value of envelope (i.e., the maximum peak) directly corresponds to the echo amplitude, $\beta_1$ and travel time, $\tau_1$. Initializations for subsequent models used in the inversion (e.g., M=≥2) are set by equally distributing their positions between the position of the maximum peak and the end of the inversion window.

When working with the first model order (e.g., M=1), echo amplitude and travel time can be found as follows:

$$(\tau_1, \beta_1) = \text{argmax} |H(S_{win})| \qquad (18)$$

Additionally, when working with higher model orders (e.g., M≥2), a time step, $\tau_{step}$, can be used. The time step is defined in Eqn. (19) below. The time step is used to equally distribute the remaining model positions as defined by Eqn. (20) below between the location of the maximum peak and the end of the inversion window, $L_{inv}$. The value of the Hilbert envelope is used to set the initial amplitudes at these distributed points, which are defined by Eqn. (21) below. For k=2:M, $$\tau_{step} = \frac{L_{inv} - \tau_1}{M - 1} \qquad (19)$$

$$\tau_k = \tau_1 + k\tau_{step} \qquad (20)$$

$$\beta_k = |H(S_{win}(\tau_k))| \qquad (21)$$

Center Frequency and Bandwidth

Figure 11:
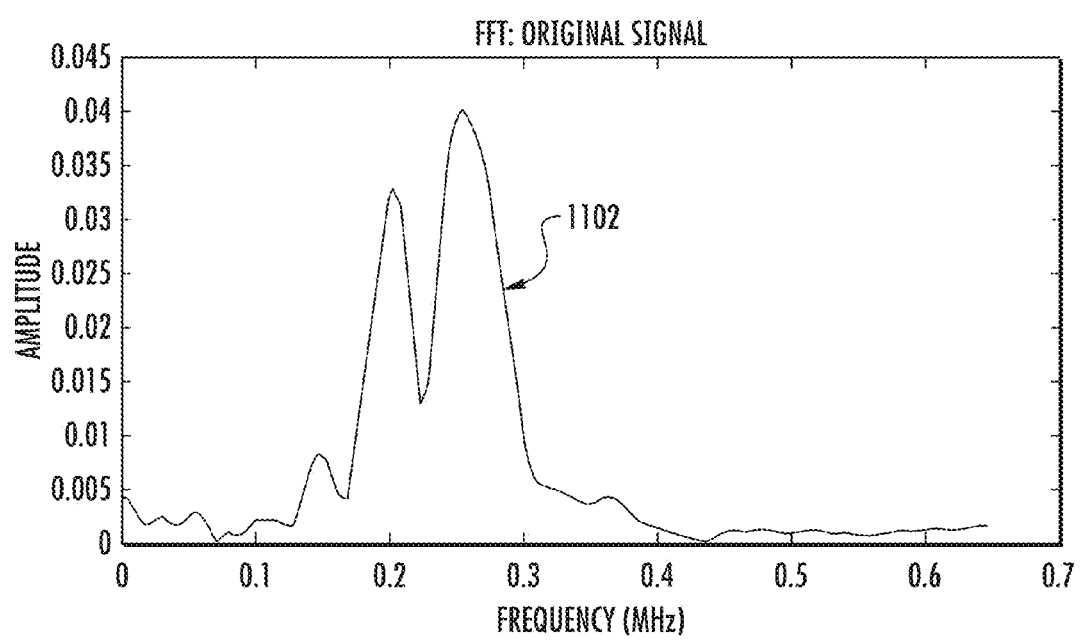
FIG. 11 is a graph illustrating the FFT of a windowed portion of an example ultrasonic signal.

The estimate for the central frequency parameter, $f_c$, can be set from the FFT of the windowed signal. For instance, an FFT of the windowed portion of the ultrasonic signal can be calculated. The FFT of the windowed portion of the ultrasonic signal of FIG. 7A is shown in FIG. 11. The maximum value of the FFT 1102 can be selected as the central frequency of the ultrasonic echo that is to be parameterized. As shown in FIG. 11, the maximum value or peak of the FFT 1102 occurs at approximately 255 kHz. It should be understood that this also approximately corresponds to the frequency of the ultrasonic transducer discussed above with regard to FIG. 7A. Additionally, when parameterization with a model order of 2 or higher is used, then the same central frequency can be used to seed the subsequent model orders up to the maximum model order ($M_{max}$) in the inversion. Because the FFT does not provide time localization in regards to where the frequencies exist, all of the models in the inversion are initialized with the same central frequency. It should be understood that using the same central frequency for the initial central frequency parameter for the higher model orders is sufficient because the other frequencies that compose the echo (e.g., ringing) are also near the maximum frequency of the ultrasonic transducer. Eqn. (22) below can be used to select the initial central frequency parameter. For k=1:M, $$f_{c_k} = \mathrm{argmax}(\mathrm{FFT}(S_{win})) \qquad (22)$$

The estimate for the initial bandwidth factor parameter, $a_k$, can also be set from the FFT of the windowed signal. Similar to the central frequency, the bandwidth can be selected using on the maximum value or peak 1102 of the FFT. To determine the approximate bandwidth of the ultrasonic echo, the derivatives to the left and right of the maximum value in the FFT can be computed until a sign change is observed. A minimum is indicated when the derivative become positive. Then, on both the left and right sides of the maximum peak of the FFT, the minimum points are subject to a linear fitting that extends downwards toward the x-axis. The squared distance between the left and right minimum points on the x-axis can be used as the bandwidth parameter estimate. It should be understood that the same bandwidth factor can be used for the estimate for all model orders. Eqn. (23) below can be used to select the initial bandwidth parameter. For k=1:M, $$a_k = (f_{o_1} - f_{o_2})^2 \qquad (23)$$

Phase

The initial estimate for the phase parameter, $\phi$, can be set to zero for all model orders. The reasoning is for this estimate is discussed below. First, if the ultrasonic echo is composed of a single clean pulse, it might be possible to accurately calculate the instantaneous phase. However, the ultrasonic echo is typically composed of multiple overlapping components. The other initial model parameters discussed above are set by initial estimate, which carries with it a certain error with no notions of how much overlap exists between them. Therefore, it is difficult to estimate a phase that is close to the optimal. Second, because phase is cyclic and parameterization convergence is insensitive to its value, it is suitable to set the initial phase at zero.

Inversion

After the main echo contained in ultrasonic signal has been localized and windowed, it is possible to invert for a plurality of echo parameters. As discussed above, the Gauss-Newton process can be integrated into an expectation maximization algorithm (EM) algorithm. The EM algorithm has a structure where at each step the expected signals are computed using the current estimate of the parameter vector and the observed data (e.g., the ultrasonic signal). Then, the corresponding parameter sets are computed using those expected signals. Alternatively, it is possible to update the parameter vector after the maximization step (e.g., the M-step). By doing so, the current parameter estimation is integrated into the E-step with the objective of speeding up convergence. This alternative method is known as the space-alternating generalized EM (SAGE) algorithm. Compared to traditional EM algorithms, the SAGE algorithm possesses a faster convergence property.

Figure 12:
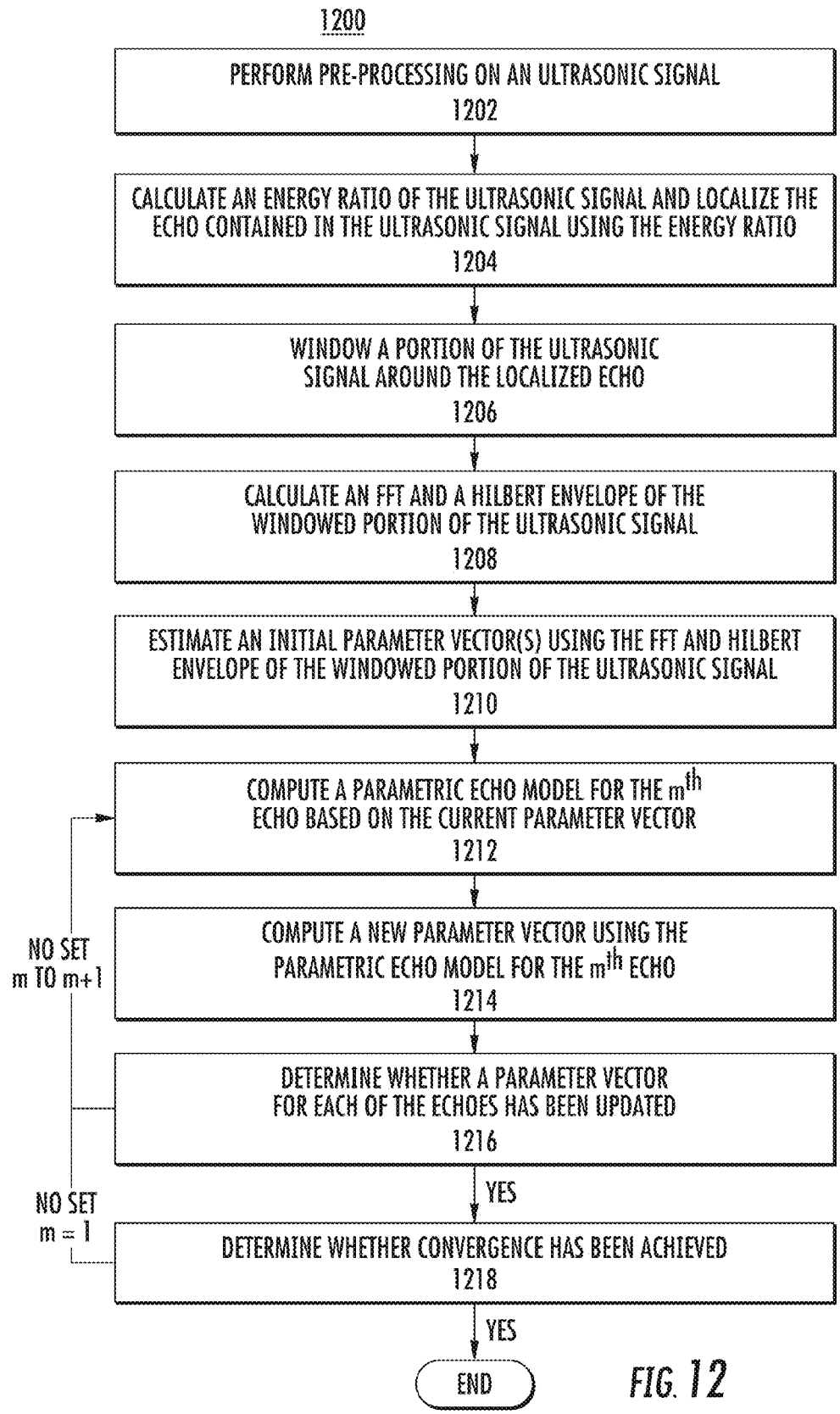
FIG. 12 is a flow diagram illustrating example operations for automatically characterizing an echo contained in an ultrasonic signal.

Referring now to FIG. 12, a flow diagram illustrating example operations 1200 for automatically characterizing an echo contained in an ultrasonic signal are shown. As discussed above, an ultrasonic signal can be generated with an ultrasonic transducer. After reflecting from a reflector, data corresponding to the ultrasonic signal can be received with the ultrasonic transducer. Optionally, the ultrasonic transducer can be located in a fluid-filled borehole, and the ultrasonic signal can be reflected from a formation. Optionally, the data corresponding to the ultrasonic signal can be pre-processed, e.g., filtered, to remove or reduce trend and/or extraneous noise. The data can be pre-processed according to any of the techniques described herein.

It should be appreciated that the logical operations described herein with respect to the various figures may be implemented (1) as a sequence of computer implemented acts or program modules (i.e., software) running on a computing device, (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Optionally, at 1202, an ultrasonic signal can be pre-processed, e.g., filtered, to remove or reduce trend and/or extraneous noise, as discussed above. At 1204, an energy ratio of the ultrasonic signal can be calculated and the echo contained in the ultrasonic signal can be localized using the energy ratio. The energy ratio can be calculated and the echo can be localized according to any of the techniques discussed herein. At 1206, a portion of the ultrasonic signal can be windowed around the localized echo. The ultrasonic signal can be windowed according to any of the techniques discussed herein. At 1208, an FFT and a Hilbert envelope of the windowed portion of the ultrasonic signal can be calculated. Then, at 1210, the initial inversion parameters (e.g., the initial parameter vectors, $\theta = [\theta_1^{(0)}; \theta_2^{(0)}; \ldots; \theta_m^{(0)}])$ can be estimated from the FFT and Hilbert envelop of the windowed portion of the ultrasonic signal. It should be understood that the iteration number and echo number can be initially set to 0 (e.g., k=0 and m=0). At 1212, the parametric echo model (e.g., the expected ultrasonic signal) for the $m^{th}$ echo can be computed based on the current parameter vector ($\theta_m^k$) and observed data y (e.g., the ultrasonic signal), for example, according to $$\hat{x}_m^k = s(\theta_m^k) + \frac{1}{M}\left\{y - \sum_{l=1}^{M} s(\theta_m^k)\right\}.$$

Step 1212 can be referred to as the Expectation Step. At 1214, using the parametric echo model computed above, a new parameter vector ($\theta_m^{k+1}$) can be computed, for example, as the maximum likelihood estimate (MLE) for ($\theta_m^k$). For example, the new parameter vector can be determined according to $\theta_m^{k+1} = \mathrm{arg}_{\theta_m} \min \|\hat{x}_m^k - s(\theta_m)\|^2$. Step 1214 can be referred to as the Maximization Step. In other words, the Maximization Step corresponds to the MLE of a single echo with the parametric echo model for the $m^{th}$ echo, e.g., $\hat{x}_m^k$. Then, in the next Expectation Step, the parametric echo model for the next signal or the $m^{th}+1$ echo, e.g., $\hat{x}_{m+1}^k$ can be computed using the recently updated parameter vector ($\theta_m^{k+1}$). At 1216, a determination is made as to whether the parameter vector for each of the echoes has been updated. If NO, m is set to m+1, and the process returns to step 1212. If YES (e.g., m>M), the process continues to step 1218, where a determination is made as to whether the convergence is achieved, e.g., $\|\theta^{k+1}-\theta^k\| \le a$ predetermined tolerance. In other words, a determination is made as to whether a change in the parameter vector between the current and previous iteration is less than a predetermined tolerance. If YES, the process ends and the plurality of echo parameters have been computed. If NO, the process continues to step 1212, e.g., m is set to 1 and k is set to k+1. Accordingly, it is possible to iterate until the convergence criterion is achieved.

EXAMPLES

Parameterization Process on Real Data

Real Data (Single Trace)

To demonstrate the result of the parameterization algorithm on a real-world borehole dataset acquired in the field, well test data has been used. The data set is comprised of 1148 traces consisting of 512 samples each at a sampling rate of 3 MHz. A sample from this dataset has been chosen to be parameterized using three Gaussian echoes (M=3). FIGS. 13A-13G illustrate the results of ultrasonic echo parameterization using three Gaussian echoes on example borehole data. FIG. 13A is a table illustrating the optimal parameters for each of the Gaussian echoes obtained by the inversion process. FIG. 13B is a graph illustrating the ultrasonic signal measured by the ultrasonic transducer arranged in the borehole. FIG. 13C is a graph illustrating the ultrasonic signal reconstructed using the Gaussian echoes. FIG. 13D is a graph illustrating the difference between the measured and reconstructed ultrasonic signals of FIGS. 13B and 13C, respectively. FIGS. 13E-13G are graphs illustrating each of the Gaussian echoes. Additionally, FIG. 14 is a graph illustrating a magnified view of the parameterization shown in FIG. 13C, e.g., a windowed portion of the ultrasonic signal.

Real Data (Multiple Traces)

Figure 15A:
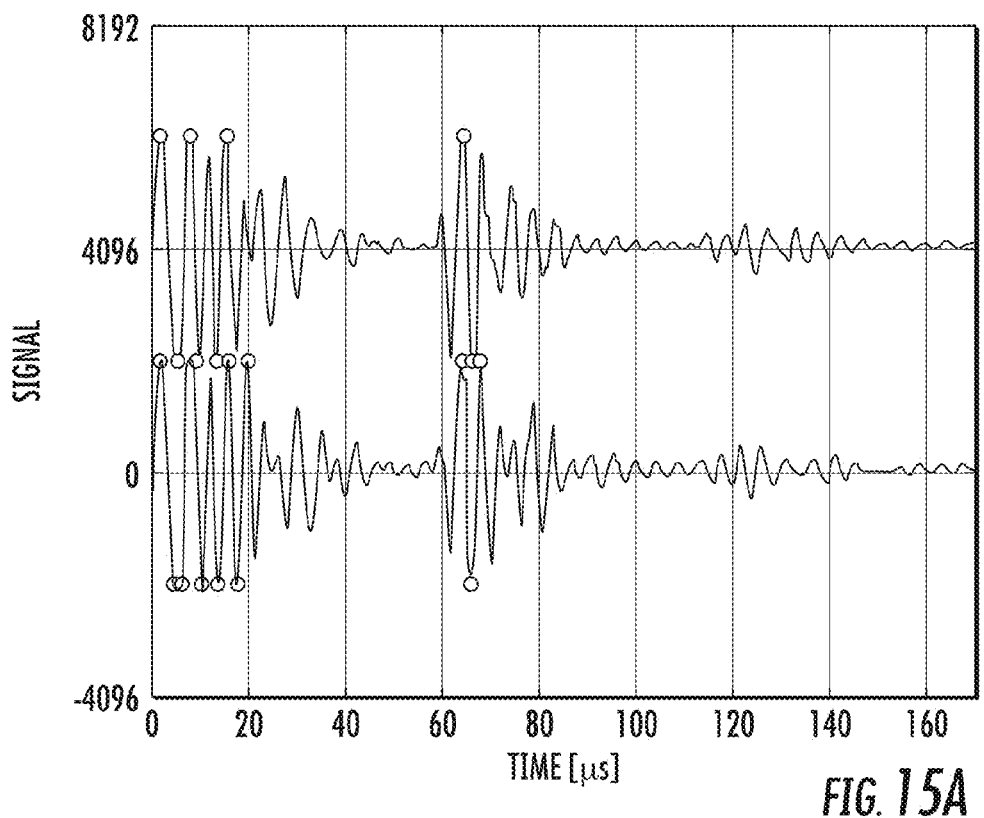
FIG. 15A is a graph illustrating an example trace containing an evident first echo arrival.
Figure 15B:
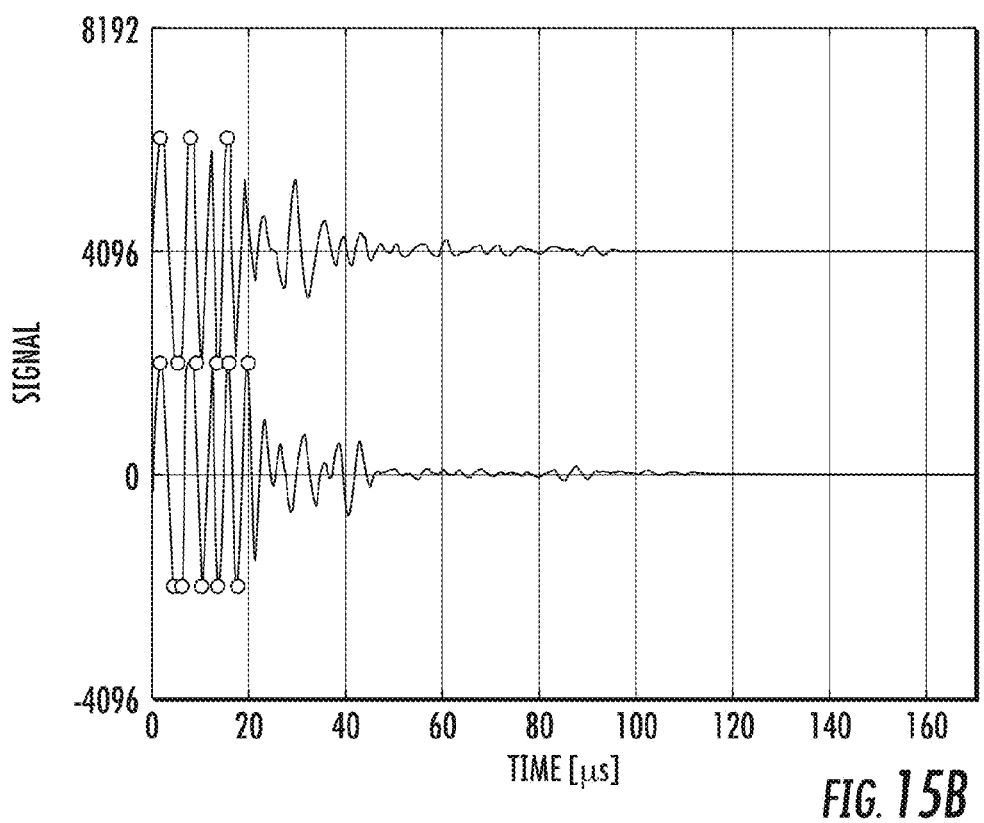
FIG. 15B is a graph illustrating an example trace without an evident first echo arrival.
Figure 16A:
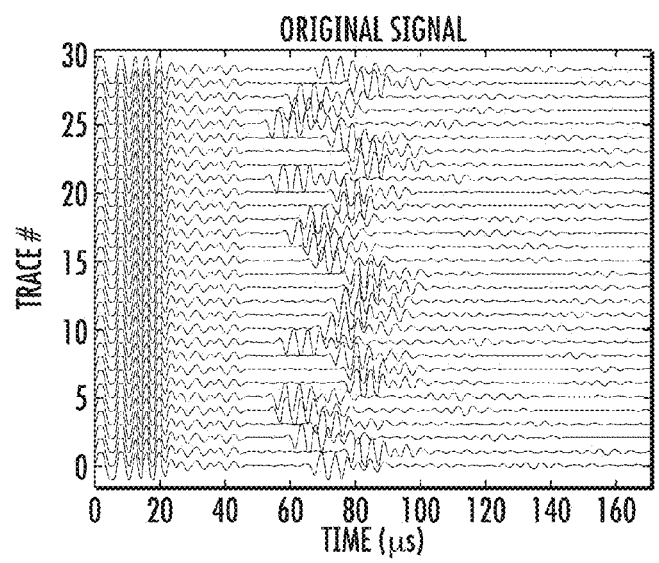
FIG. 16A is a graph illustrating multiple ultrasonic signals measured in a borehole.
Figure 16B:
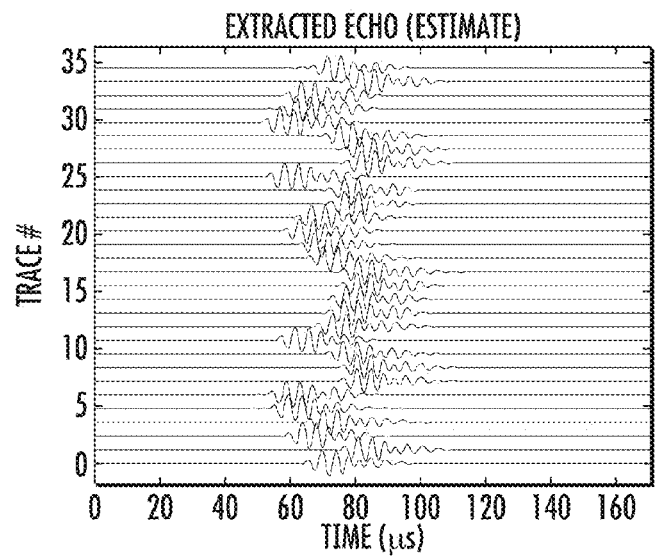
FIG. 16B is a graph illustrating the echoes of the ultrasonic signals of FIG. 16A estimated by the parameterization process.
Figure 16C:
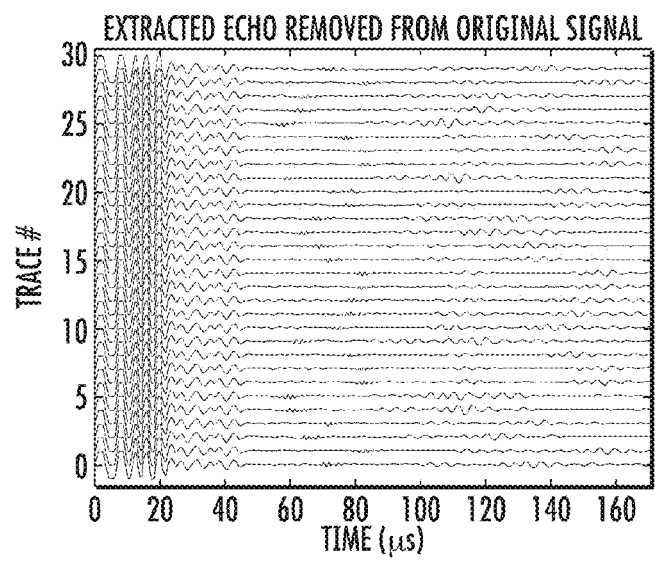
FIG. 16C is a graph illustrating the portions of the measured ultrasonic signals of FIG. 16A after removing the extracted echoes of FIG. 16B.

To apply the parameterization process on a large-scale data set, the rest of the traces in the borehole-acquired dataset were subject to parameterization to specifically test the robustness of the localization and windowing functions. In the 1148 trace dataset, 95% of the traces contain an evident first echo arrival. FIG. 15A is a graph illustrating an example trace containing an evident first echo arrival. In the remaining 5% of the traces, there is an apparent firing pulse however no echo arrives. FIG. 15B is a graph illustrating an example trace that does not contain an evident first echo arrival. In 95% of the cases where a first echo is evident, the parameterization algorithm successfully localized, windowed and inverted for the first echo (e.g., 2% accuracy of parameterization with roughly 30 iterations/1 ms of processing time using M=3). In the cases where no echo was evident, the excitation pulse was windowed and parameterized. FIG. 16A is a graph illustrating multiple ultrasonic signals measured in a borehole. FIG. 16B is a graph illustrating the echoes of the ultrasonic signals of FIG. 16A estimated by the parameterization process. FIG. 16C is a graph illustrating the portions of the measured ultrasonic signals of FIG. 16A after removing the extracted echoes of FIG. 16B.

Echo Extraction from a Noisy Baseline

Figure 17A:
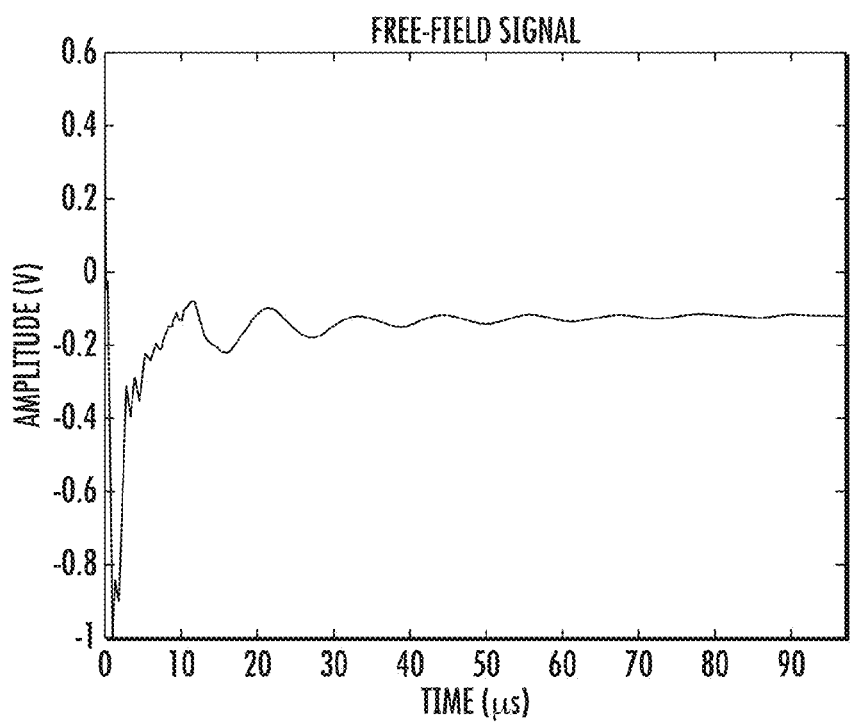
FIG. 17A is a graph illustrating ultrasonic transducer free-field response.
Figure 17B:
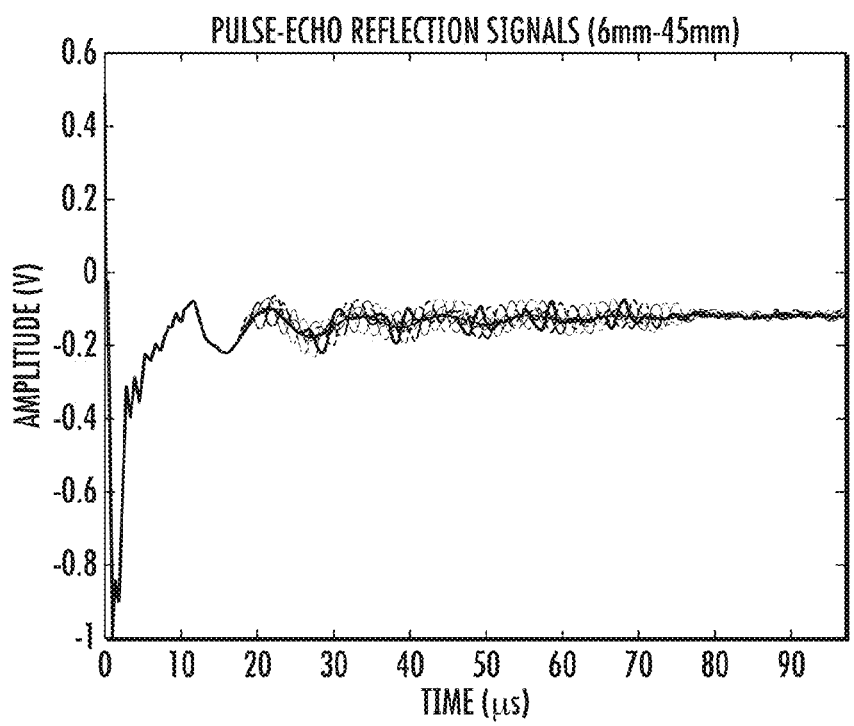
FIG. 17B is a graph illustrating the observed pulse-echo responses from 6 mm to 45 mm.

To test the effectiveness of the algorithm in extracting the initial echo parameters from the baseline in one shot, pulse-echo lab data that had been acquired with an aluminum reflector at stand-offs varying from 6 mm to 45 mm were used. FIG. 17A is a graph illustrating ultrasonic transducer free-field response. FIG. 17B is a graph illustrating the observed pulse-echo responses from 6 mm to 45 mm. As shown in FIGS. 17A-17B, there is an inherent ringing of the ultrasonic transducer, which obscures the arriving echo at varying levels of severity as the stand-off decreases. To compare the accuracy of the parameterization, the true free-field response of the ultrasonic transducer has also been recorded, which is shown in FIG. 17A. For verification, the true free-field response can be subtracted from the observed trace that is contaminated with the baseline to get the true-echo. The value of the arrival time as well as the amplitude of this echo can be compared to this true echo to gauge how accurately the obscured echo is extracted.

Referring now to FIGS. 18A-18F, graphs illustrating the decomposition of an ultrasonic signal are shown. The ultrasonic signal is recorded 8 mm away from the reflector. The ultrasonic signal is detrended (e.g., using a two-piece linear fitting), gated and then parameterized. To illustrate the result of the parameterization, a recorded waveform using a reflector situated 8 mm away from the ultrasonic transducer is used. At this reflector distance the ringing baseline significantly contaminates the arriving echo. The objective is to cleanly extract the echo from this baseline.

The trace is first pre-preprocessed by removing the exponential trend, gated and parameterized using a model order of 3 (M=3). The detrended and gated signal is shown in FIG. 18A. FIG. 18B is a graph illustrating the parametric reconstruction as compared to the detrended and gated signal in FIG. 18A. As shown in FIG. 18B, the parameterization approximates the detrended and gated signal well, which is also indicated by FIG. 18C illustrating difference between the detrended and gated signal and the parametric reconstruction. In the region of interest (e.g., the location of the main peak and trough of the arriving echo), the error is around 1%. FIGS. 18D-18F are graphs illustrating the composition of the reconstruction. Of the three models that compose the reconstruction, the first model (#1), happens to be of the highest amplitude. The remaining two echoes (Model #2 and Model #3) are used to represent the baseline (as this portion of the signal is not as well suited to the Gaussian empirical model as the echo hidden within).

Figure 19A:
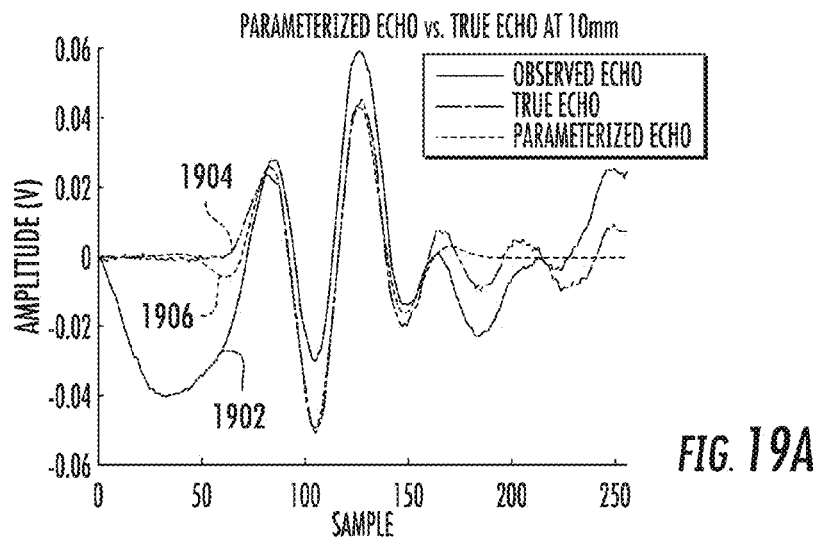
FIGS. 19A-19C are graphs illustrating the comparison between a true echo produced by conducting a parameterization using a model order of 2 (M=2) on traces recorded with an ultrasonic transducer at 10 mm, 20 mm and 30 mm of stand-off.
Figure 19B:
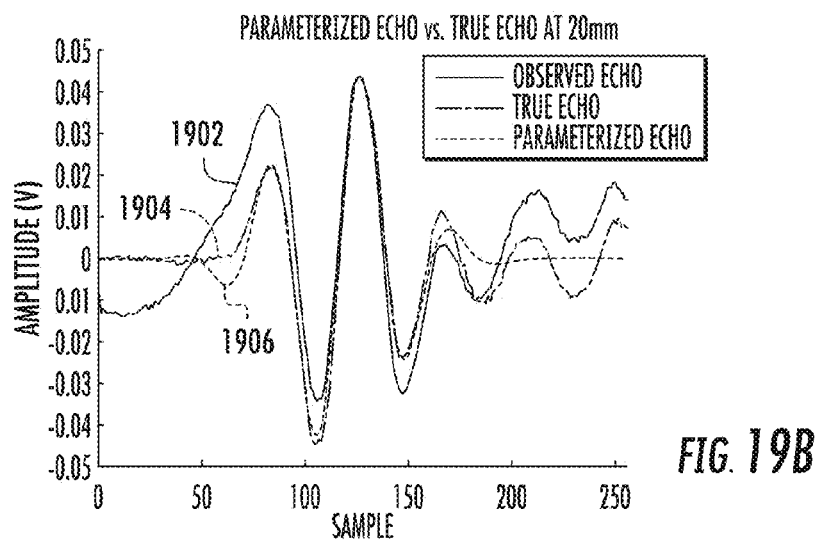
Figure 19C:
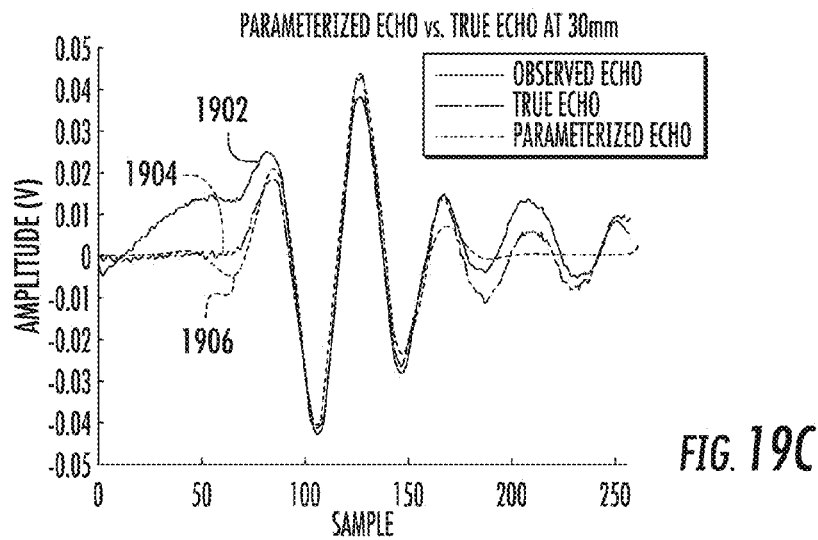

Since the first model that composes the parameterization is taken to be the true echo, it is desirable to determine how well it compares to the actual echo. For this comparison, the baseline from the signal is removed by subtracting the measured free-field response of the transducer. FIGS. 19A-19C are graphs illustrating the comparison between a true echo produced by conducting a parameterization using a model order of 2 (M=2) on traces recorded by an ultrasonic transducer at 10 mm, 20 mm and 30 mm of stand-off. The true echo 1906 is determined by subtracting the ultrasonic transducer's free-field response from the observed echo 1902. The model or parameterized echo 1904 that exhibits the highest amplitude is selected as the echo component. From the originally observed gated signals, directly deducing the amplitude and shape of the hidden echo can be difficult, but after parametric extraction, the true echo can be clearly revealed. As shown in FIGS. 19A-19C, the parameterized echo 1904 overlays well with the true echo response 1906. In all cases, error in the main peaks and troughs of the echo does not exceed 5%, even at near standoffs (10 mm away from the reflector) where they are significantly obscured by the ringing baseline.

Imaging Tests

To demonstrate the effectiveness of the parameterization process in terms of imaging parameterization is compared to direct parameter extraction using filtering.

Figure 20:
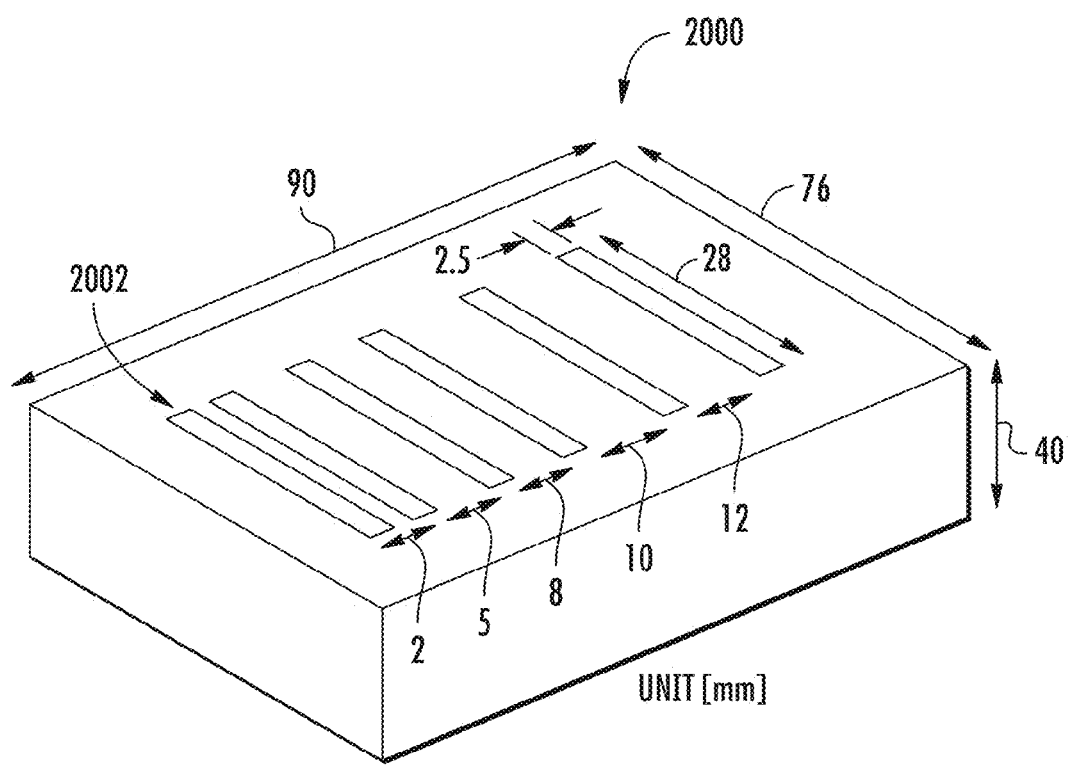
FIG. 20 is a limestone block used in imaging tests according to implementations discussed herein.

Referring now to FIG. 20, a limestone block 2000 (90 mm×76 mm×40 mm) used in imaging tests according to implementations discussed herein is shown. For the data set, the limestone block 2000 with six slits (2.5 mm×28 mm) 2002 with varying spacing, e.g., 2 mm, 5 mm, 8 mm, 10 mm, and 12 mm as shown, was immersed in water and scanned at a stand-off of 20 mm in the horizontal plane parallel to the face of the block. The scan was conducted in 1 mm increments covering 119 mm×95 mm (e.g., 11305 samples). The central frequency of the ultrasonic transducer was approximately 375 MHz.

The data set was processed in two ways: first using parameterization and secondly utilizing a filtering method where the parameters are directly extracted from the observed traces after the application of a band-pass filter centered near the transducers central frequency. In both methods, images were produced using five key attributes of the echo (e.g., travel time, amplitude, bandwidth (or curvature, in the case of filtering), center frequency, and phase).

Figure 21A:
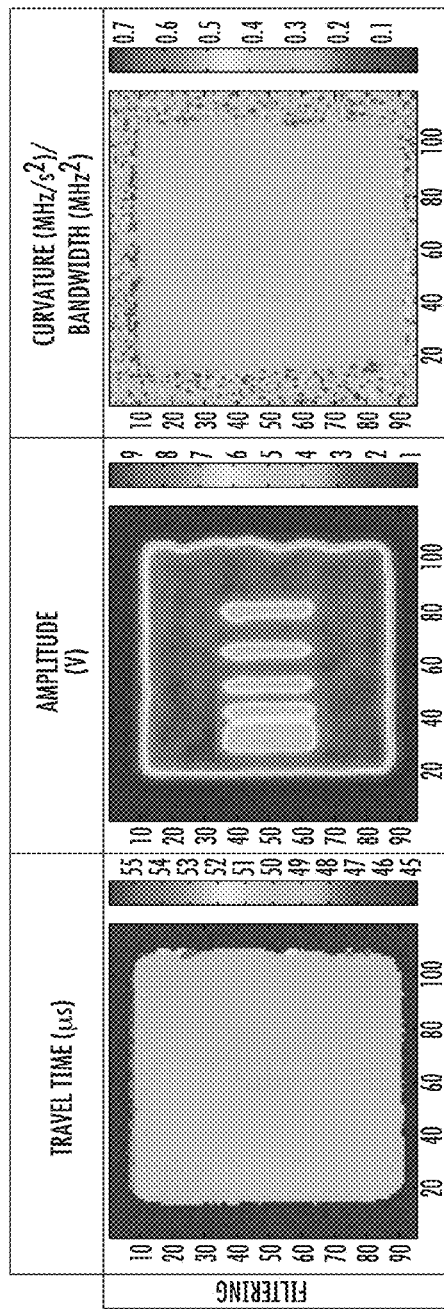
FIGS. 21A-21D are the imaging results for filtering and parameterization, respectively.
Figure 21B:
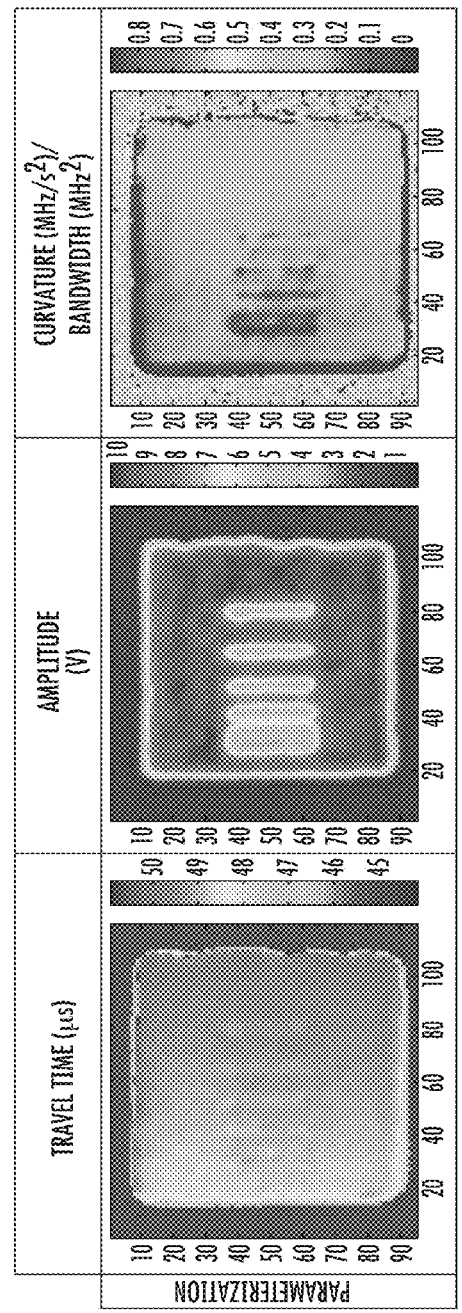
Figure 21C:
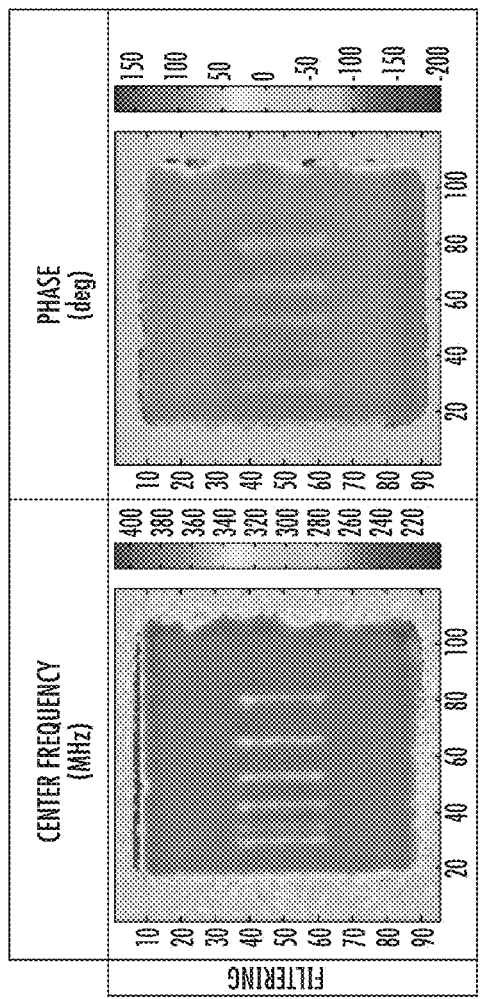
Figure 21D:
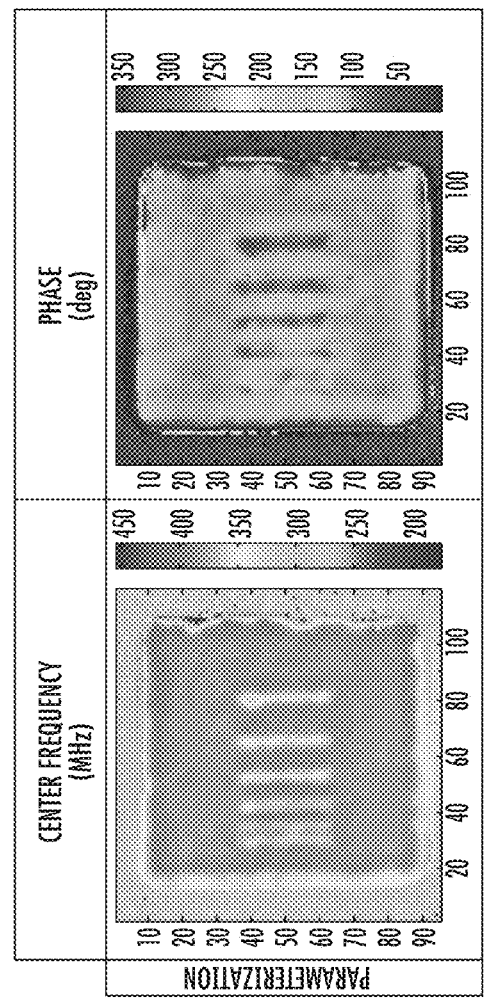

FIGS. 21A-21B are the imaging results for filtering and parameterization, respectively. Because the ultrasonic transducer is operated under ambient pressure, coupling is not optimal resulting in ringing and relatively small arriving echo amplitudes. Unlike filtering, parameterization utilizes the entire signal in the gate to estimate the echo parameters which results in utilizing more of the signal as time-support in forming the parameter estimate. The merits of this are evident in all five graphs. In general, the images produced from echoes characterized through parameterization can resolve more detail in comparison to filtering. Unlike filtering, parameterization uses the entire signal in the window to estimate the echo parameters. The merits of this are evident in all five graphs. The color scales of all images have been kept the same so that the images are displayed with a similar dynamic range.

When examining the image produced by the travel time of the echo, it is evident that the block was not exactly parallel to the ultrasonic transducer during the scan. Using parameterization to extract the arrival time, this is clearly visible as the color gradually fades (indicating an increase in travel time due to tilt). The filtered image has a small color gradation but the detail of the slits is not as noticeable. In terms of amplitude, the results look similar but with parameterization the definition of the left-most slit is much more visible. When comparing the images generated by bandwidth (or in the case of filtering, curvature), the regions with the two left-most closely spaced slits were resolved with significantly more detail using parameterization. Of all the parametric attributes, the central frequency is most sensitive to small changes in the scanned formation as is evidenced by the two most closely spaced slits being resolved. Using filtering, the center frequency image is grainy and lacks some contrast whereas using the parametric method, the details in the image are more pronounced (especially in the contrast of the slits as well as the revealing some of the block's surface texture). Finally, images using phasing of the arriving echo look similar, but the image produced by parameterization features superior contrast.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claimed subject matter.

What is claimed:

1. A method to image a formation by automatically characterizing an echo contained in an ultrasonic signal, the ultrasonic signal being generated with an ultrasonic transducer, the method comprising:
   a. receiving data corresponding to the ultrasonic signal with the ultrasonic transducer of a downhole acoustic tool;
   b. calculating an energy ratio of the ultrasonic signal and localizing the echo contained in the ultrasonic signal using the energy ratio; comprising;
      b1. calculating an energy ratio function of the ultrasonic signal, wherein the energy ratio function is $$E_x = a_1 \left( \frac{\sum_{i=x+1}^{x+L} E_i}{\sum_{i=x-L}^{x-1} E_i} \right) / (1 + a_2 E_{total}),$$

where $E_x$ is energy at a given data point, $a_1$ and $a_2$ are energy adjustment factors, L is a window length, $$\sum_{i=x+1}^{x+L} E_i$$

is signal energy, $$\sum_{i=x-L}^{x-1} E_i$$

is noise energy and $E_{total}$ is total energy; and
      b2. identifying a maximum value of the energy ratio function of the ultrasonic signal, wherein the maximum value corresponds to an approximate location of the echo contained in the ultrasonic signal;
   c. windowing a portion of the ultrasonic signal around the localized echo;
   d. calculating a Fast Fourier Transform (FFT) and a Hilbert envelop of the windowed portion of the ultrasonic signal;
   e. estimating M echo parameter vectors from the FFT and the Hilbert envelope of the windowed portion of the ultrasonic signal, wherein each of the M echo parameter vectors comprises a plurality of echo parameters;
   f. calculating M parametric echo models based on each of the M echo parameter vectors; and
   g. iteratively minimizing a difference between the windowed portion of the ultrasonic signal and a sum of the M parametric echo models;
   transmitting parameters from the M parametric echo models for use in characterizing the formation.

2. The method of claim 1, wherein calculating an energy ratio function of the ultrasonic signal comprises:
   b3. reversing the data corresponding to the ultrasonic signal from a forward order to a reversed order;
   b4. calculating the energy ratio function of the reversed ultrasonic signal; and b5. identifying a maximum value of the energy ratio function of the reversed ultrasonic signal, wherein the maximum value of the energy ratio function of the ultrasonic signal corresponds to a left break of a first echo contained in the ultrasonic signal and the maximum value of the energy ratio function of the reversed ultrasonic signal corresponds to a right break of the first echo contained in the ultrasonic signal.

3. The method of claim 1, wherein calculating an energy ratio function of the ultrasonic signal comprises:
  b3. cropping the data corresponding to the ultrasonic signal;
  b4. calculating the energy ratio function of the cropped ultrasonic signal; and
  b5. identifying a maximum value of the energy ratio function of the cropped ultrasonic signal, wherein the maximum value of the energy ratio function of the ultrasonic signal corresponds to a left break of a first echo contained in the ultrasonic signal and the maximum value of the energy ratio function of the cropped ultrasonic signal corresponds to a left break of a second echo contained in the ultrasonic signal.

4. The method of claim 1, wherein the window length (L) is approximately equal to $$s \frac{f_s}{f_c},$$

where s is a tuning coefficient, $f_c$ is a center frequency of the echo of the ultrasonic signal, and $f_s$ is a sampling frequency.

5. The method of claim 1, wherein windowing a portion of the ultrasonic signal around the localized echo comprises applying a half-Hanning taper to data corresponding to one or more sides of the ultrasonic signal outside of the windowed portion of the ultrasonic signal around the localized echo.

6. The method of claim 1, wherein iteratively minimizing a difference between the windowed portion of the ultrasonic signal and a sum of the M parametric echo models comprises performing at least one of a Gauss-Newton (GN) optimization, a genetic algorithm (GA) and an evolutionary optimization meta-heuristic approach.

7. The method of claim 1, wherein calculating M parametric echo models comprises calculating M parametric echo models based on each of the M echo parameter vectors and the windowed portion of the ultrasonic signal, and wherein iteratively minimizing a difference between the windowed portion of the ultrasonic signal and a sum of the M parametric echo models comprises:
  h. determining the plurality of echo parameters for each of the M echo parameter vectors based on each of the M parametric echo models;
  i. updating the M echo parameter vectors;
  j. determining if the updated M echo parameter vectors converge with the M echo parameter vectors; and
  k. if convergence is not achieved, calculating M parametric echo models based on each of the updated M echo parameter vectors and the windowed portion of the ultrasonic signal and repeating steps (h)-(k).

8. The method of claim 1, further comprising filtering the data corresponding to the ultrasonic signal to remove at least one baseline component of the ultrasonic signal.

9. The method of claim 1, wherein the plurality of echo parameters comprise at least one of a bandwidth factor ($\alpha$), an arrival time ($\tau$), a center frequency ($f_c$), a phase ($\phi$), an amplitude ($\beta$), and combinations thereof.

10. The method of claim 9, further comprising generating an image using the plurality of echo parameters.

11. A system to image a formation by automatically characterizing an echo contained in an ultrasonic signal of a downhole acoustic tool, comprising:
  an ultrasonic transducer configured to generate and receive an ultrasonic signal; and
  a control unit comprising at least one processor and a memory, wherein the control unit is configured to:
  a. receive data corresponding to the ultrasonic signal from the ultrasonic transducer;
  b. calculate an energy ratio of the ultrasonic signal and localize an echo contained in the ultrasonic signal using the energy ratio, the energy ratio comprising;
    b1. calculating an energy ratio function of the ultrasonic signal, wherein the energy ratio function is $$E_x = a_1 \left( \frac{\sum_{i=x+1}^{x+L} E_i}{\sum_{i=x-L}^{x-1} E_i} \right) / (1 + a_2 E_{total}),$$

where Ex is energy at a given data point, $a_1$ and $a_2$ are energy adjustment factors, L is a window length, $$\sum_{i=x+1}^{x+L} E_i$$

is signal energy, $$\sum_{i=x-L}^{x-1} E_i$$

is noise energy and $E_{total}$ is total energy; and
    b2. identifying a maximum value of the energy ratio function of the ultrasonic signal, wherein the maximum value corresponds to an approximate location of the echo contained in the ultrasonic signal;
  c. window a portion of the ultrasonic signal around the localized echo;
  d. calculate a Fast Fourier Transform (FFT) and a Hilbert envelop of the windowed portion of the ultrasonic signal;
  e. estimate M echo parameter vectors from the FFT and the Hilbert envelope of the windowed portion of the ultrasonic signal, wherein each of the M echo parameter vectors comprises a plurality of echo parameters;
  f. calculate M parametric echo models based on each of the M echo parameter vectors; and
  g. iteratively minimize a difference between the windowed portion of the ultrasonic signal and a sum of the M parametric echo models;
  transmitting parameters from the M parametric echo models for use in characterizing the formation.

12. The system of claim 11, wherein the control unit is configured to calculate an energy ratio function of the ultrasonic signal by:

b3. reversing the data corresponding to the ultrasonic signal from a forward order to a reversed order;

b4. calculating the energy ratio function of the reversed ultrasonic signal; and b5. identifying a maximum value of the energy ratio function of the reversed ultrasonic signal, wherein the maximum value of the energy ratio function of the ultrasonic signal corresponds to a left break of a first echo contained in the ultrasonic signal and the maximum value of the energy ratio function of the reversed ultrasonic signal corresponds to a right break of the first echo contained in the ultrasonic signal.

13. The system of claim 11, wherein the control unit is configured to calculate an energy ratio function of the ultrasonic signal by:

b3. cropping the data corresponding to the ultrasonic signal;

b4. calculating the energy ratio function of the cropped ultrasonic signal; and b5. identifying a maximum value of the energy ratio function of the cropped ultrasonic signal, wherein the maximum value of the energy ratio function of the ultrasonic signal corresponds to a left break of a first echo contained in the ultrasonic signal and the maximum value of the energy ratio function of the cropped ultrasonic signal corresponds to a left break of a second echo contained in the ultrasonic signal.

14. The system of claim 11, wherein the control unit is configured to window a portion of the ultrasonic signal around the localized echo by applying a half-Hanning taper to data corresponding to one or more sides of the ultrasonic signal outside of the windowed portion of the ultrasonic signal around the localized echo.

15. The system of claim 11, wherein the control unit is configured to iteratively minimize a difference between the windowed portion of the ultrasonic signal and a sum of the M parametric echo models by performing at least one of a Gauss-Newton (GN) optimization, a genetic algorithm (GA) and an evolutionary optimization meta-heuristic approach.

16. The system of claim 11, wherein the control unit is configured to calculate M parametric echo models by calculating M parametric echo models based on each of the M echo parameter vectors and the windowed portion of the ultrasonic signal, and wherein the control unit is configured to iteratively minimize a difference between the windowed portion of the ultrasonic signal and a sum of the M parametric echo models by:

h. determining the plurality of echo parameters for each of the M echo parameter vectors based on each of the M parametric echo models;

i. updating the M echo parameter vectors;

j. determining if the updated M echo parameter vectors converge with the M echo parameter vectors; and k. if convergence is not achieved, calculating M parametric echo models based on each of the updated M echo parameter vectors and the windowed portion of the ultrasonic signal and repeating steps (h)-(k).

17. The system of claim 11, wherein the plurality of echo parameters comprise at least one of a bandwidth factor ($\alpha$), an arrival time ($\tau$), a center frequency ($f_c$), a phase ($\phi$), an amplitude ($\beta$), and combinations thereof.

18. The system of claim 17, wherein the control unit is further configured to generate an image using the plurality of echo parameters.

* * * * *